(12) United States Patent
Hariyama et al.

(10) Patent No.: US 9,557,253 B2
(45) Date of Patent: Jan. 31, 2017

(54) ELECTRON MICROSCOPIC OBSERVATION METHOD FOR OBSERVING BIOLOGICAL SAMPLE IN SHAPE AS IT IS, AND COMPOSITION FOR EVAPORATION SUPPRESSION UNDER VACUUM, SCANNING ELECTRON MICROSCOPE, AND TRANSMISSION ELECTRON MICROSCOPE USED IN THE METHOD

(75) Inventors: Takahiko Hariyama, Shizuoka (JP); Yasuharu Takaku, Shizuoka (JP); Hiroshi Suzuki, Shizuoka (JP); Yoshinori Muranaka, Shizuoka (JP); Isao Ohta, Shizuoka (JP); Masatsugu Shimomura, Miyagi (JP); Daisuke Ishii, Aichi (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 527 days.

(21) Appl. No.: 14/343,537
(22) PCT Filed: Sep. 7, 2012
(86) PCT No.: PCT/JP2012/072982
§ 371 (c)(1),
(2), (4) Date: Apr. 16, 2014
(87) PCT Pub. No.: WO2013/035866
PCT Pub. Date: Mar. 14, 2013

(65) Prior Publication Data
US 2014/0227734 A1    Aug. 14, 2014

(30) Foreign Application Priority Data

Sep. 9, 2011 (JP) ................................. 2011-197685
Feb. 29, 2012 (JP) ................................. 2012 044383

(51) Int. Cl.
*H01J 37/00* (2006.01)
*G01N 1/44* (2006.01)
(Continued)

(52) U.S. Cl.
CPC .............. *G01N 1/44* (2013.01); *G01N 1/2853* (2013.01); *G01N 23/04* (2013.01); *G01N 23/225* (2013.01);
(Continued)

(58) Field of Classification Search
USPC ................................ 250/306, 307, 310, 311
See application file for complete search history.

(56) References Cited

FOREIGN PATENT DOCUMENTS

| JP | 61-2250 | 1/1986 |
|---|---|---|
| JP | 61-88442 | 5/1986 |

(Continued)

OTHER PUBLICATIONS

International Search Report issued Nov. 27, 2012 in International (PCT) Application No. PCT/JP2012/072982.
(Continued)

*Primary Examiner* — Nicole Ippolito
*Assistant Examiner* — Hanway Chang
(74) *Attorney, Agent, or Firm* — Wenderoth, Lind & Ponack, L.L.P.

(57) ABSTRACT

Provided is an observation method by an electron microscope, in which a biological sample can be observed as it is alive and a situation that the biological sample is moving can be observed using an electron microscope, and a composition for evaporation suppression under vacuum, a scanning electron microscope, and a transmission electron microscope used in the method.
The sample observation method by an electron microscope according to the invention includes applying a composition for evaporation suppression containing at least one kind selected from an amphiphilic compound, oils and fats, and an ionic liquid to the surface of a sample to form a thin film, and covering the sample with the thin film, and displaying an electron microscopic image of the sample, which is covered with the thin film and accommodated in a sample chamber under vacuum, on a display device.

24 Claims, 28 Drawing Sheets

(51) Int. Cl.
*G01N 23/225* (2006.01)
*G01N 23/04* (2006.01)
*H01J 37/20* (2006.01)
*G01N 1/28* (2006.01)

(52) U.S. Cl.
CPC .......... *G01N 23/2252* (2013.01); *H01J 37/20* (2013.01); *G01N 2223/612* (2013.01); *H01J 2237/2002* (2013.01); *H01J 2237/2004* (2013.01)

(56) References Cited

FOREIGN PATENT DOCUMENTS

| | | |
|---|---|---|
| JP | 63-78116 | 6/1988 |
| JP | 10-134751 | 5/1998 |
| JP | 78116 | 6/1998 |
| JP | 2004-319518 | 11/2004 |
| JP | 2005-26530 | 1/2005 |
| JP | 2010-25656 | 2/2010 |

OTHER PUBLICATIONS

Y. Takaku et al., "A Thin Polymer Membrane, Nano-Suit, Enhancing Survival Across the Continuum Between Air and High Vacuum", PNAS, vol. 110, No. 19, pp. 7631-7635, May 7, 2013.

H. Suzuki et al., "In Situ Preparation of Biomimetic Thin Films and Their Surface-Shielding Effect for Organisms in High Vacuum", PLoS ONE, vol. 8, No. 11, p. e78563, Nov. 2013.

<EXAMPLE 3>

SS-2

Live SEM image (POLYPEDIUM VANDERPLANKI)

<EXAMPLE 4>
Live SEM image (WIGGLE TAIL)  SS-2

A terrestrial organism, for which airtightness is not sufficiently obtained only by coating with the SS solution or the like, is encapsulated in a capsule, only the observation part is put out from the capsule, and analysis thereof as it is alive is performed while preserving the air in the capsule.

<EXAMPLE 6> Live SEM image (ANT/LEG)   SS-1

<EXAMPLE 7>

Live SEM image (ORYZIAS LATIPES/SCALE)

SS-1

An aquatic organism, for which airtightness is not sufficiently obtained only by coating with the SS solution or the like, is encapsulated in a microtube, only the observation part is put out from the tube, and analysis thereof as it is alive is performed while preserving the water system of the tube.

<EXAMPLE 8> Live SEM image (FISH/FIN) SS-2

LM image      Live SEM image

<EXAMPLE 9> SS-2

Live TEM image (HYDRA SINGLE ECTODERMAL EPITHELIAL CELL)

LM image          Live TEM image

<EXAMPLE 10>
Live SEM image (PLANARIAN)   SS-3

<EXAMPLE 11>

Tween 20

Independent polymerized film (Triton™ X-100) (a, b) formed by plasma irradiation and novel SEM images of a sample coated with the film (c - f).

<EXAMPLE 12>

Triton™ X-100

<EXAMPLE 13>

Independent polymerized film (Pluronic® F-127) (a, b) formed by plasma irradiation and novel SEM images of a sample coated with the film (c - f).

Pluronic® F-127

<EXAMPLE 14>

Brij® 35

Independent polymerized film (Brij® 35) (a, b) formed by plasma irradiation and novel SEM images of a sample coated with the film (c - f).

<EXAMPLE 15>

Independent polymerized film (CHAPS) (a, b) formed by plasma irradiation and novel SEM images of a sample coated with the film (c - f).

CHAPS

<EXAMPLE 16>

Independent polymerized film (MEGA8) (a, b) formed by plasma irradiation and novel SEM images of a sample coated with the film (c - f).

MEGA8

<EXAMPLE 17>

Independent polymerized film (Sodium cholate) (a, b) formed by plasma irradiation and novel SEM images of a sample coated with the film (c - f).

Sodium cholate

Independent polymerized film (n-Dodecyl-β-D-maltoside) (a, b) formed by plasma irradiation and novel SEM images of a sample coated with the film (c - f).

<EXAMPLE 18>
n-Dodecyl-β-D-maltoside

<EXAMPLE 19> n-Octyl-β-D-glucoside

Independent polymerized film (n-Octyl-β-D-glucoside) (a, b) formed by plasma irradiation and novel SEM images of a sample coated with the film (c - f).

Independent polymerized film (1,3-Diallylimidazolium bromide) (a, b) formed by plasma irradiation and novel SEM images of a sample coated with the film (c - f).

<EXAMPLE 19>

Imidazolium salt (1,3-Diallylimidazolium bromide)

ELECTRON MICROSCOPIC OBSERVATION METHOD FOR OBSERVING BIOLOGICAL SAMPLE IN SHAPE AS IT IS, AND COMPOSITION FOR EVAPORATION SUPPRESSION UNDER VACUUM, SCANNING ELECTRON MICROSCOPE, AND TRANSMISSION ELECTRON MICROSCOPE USED IN THE METHOD

TECHNICAL FIELD

The present invention relates to an electron microscopic observation method for observing a biological sample in the shape as it is in a scanning electron microscope, a transmission electron microscope, or the like, and a composition for evaporation suppression under vacuum, a scanning electron microscope, and a transmission electron microscope used in the method.

BACKGROUND ART

A sample is put under vacuum in order to perform sample observation using a scanning electron microscope and a transmission electron microscope, and thus the sample is desired to be resistant to vacuum and to be imparted with electrical conductivity required to acquire an image thereof.

The preparation of a sample for scanning electron microscope is performed as follows. The sample is dehydrated by vacuum drying in advance, and then an electrically conducting material (platinum, carbon, gold, palladium, osmium, and the like) is coated on the surface of the sample by a means of vapor deposition, sputtering or the like in order to impart electrical conductivity and improve the generation efficiency of secondary electrons.

Materials, such as metals and semiconductors, which have electrical conductivity and resistance to vacuum, do not require such a pretreatment, but materials, which do not have electrical conductivity, requires conductive film coating by an electrically conductive material. In addition, conductive film coating by an electrically conductive material is required for materials deteriorating in resistance to vacuum, that is, materials deformed by vacuum drying or irradiation of an electron beam in a vacuum at the time of electron microscopic observation, as well.

Biological/living body samples contain a large amount of water, and thus vacuum drying in advance is required in many cases. For this reason, the surface shape thereof is significantly deformed in some cases, and thus it is difficult to observe a biological/living body sample in the living state as it is using an electron microscope.

Water-retaining state of wet samples such as gelatinous materials and foods can be observed at room temperature using a low vacuum SEM or a cryo-SEM, an environmental SEM (ESEM), and the like. According to these techniques, not only wet samples but also untreated samples can be observed. However, a high vacuum is required in order to perform observation at a high magnification, and thus the sample is required to be resistant to vacuum or electrically conductive. For that reason, it is difficult to acquire an image in the living state as it is at a high magnification in the observation of a biological/living body sample, as well.

In recent years, electron microscopic observation methods using an ionic liquid have been suggested. Patent Literature 1 and Non Patent Literature 2 disclose that a wet sample is scanning electron microscopically observed using an ionic liquid. Non Patent Literature 2 discloses the application of the method on cells, as well. In addition, Patent Literature 2 discloses a method using the technique on ionic liquids in transmission electron microscopic observation.

CITATION LIST

Patent Literature

Patent Literature 1: WO 2007/083756
Patent Literature 2: JP 2009-266741 A

Non Patent Literature

Non Patent Literature 1: Langmuir, 2011, 27, 9671-9675
Non Patent Literature 2: Microsc. Res. Tech. 2011, 74, 415-420

SUMMARY OF INVENTION

Technical Problem

However, even by the observation using an environmental SEM or the methods according to the respective documents described above, an electron microscopic image of a sample has not yet been directly acquired in a state as it is at a high magnification. In addition, with regard to biological/living body samples, it has not yet been achieved that a biological/living body sample in a living state is electron microscopically observed as it is alive.

In other words, in a biological sample, an electron microscopic observation on the situation that the biological sample is moving as it is alive has not yet been achieved.

Moreover, it has not been possible for a sample recovered after electron microscopic observation to continue to grow or live. In other words, electron microscopic observation achieving to return alive has been impossible.

The environment for electron microscopic measurement is a vacuum state and thus a sample is put in an extremely dry state. For this reason, deformation or transformation of the sample occurs and thus it is not possible to observe the sample in a state near the living state as it is.

Furthermore, in a hydrated sample, the hydrated sample is instantly frozen when put under vacuum, and cryohydrate of the sample brings about deformation or transformation of the sample. Hence, it is not possible to observe the sample in a state near the original state.

In a biological sample, since the biological sample is put under vacuum, oxygen supply from the outer system is interrupted and thus the sample falls into hypoxia. In addition, the biological sample is put in a dry state, and thus becomes like a dried fish (a squid becomes like a dried squid). As a result, it is difficult for a biological sample to be in the living state as it is in the microscope body of an electron microscope.

Even a living being, which is capable of withstanding a dry state, perishes before or during observing the situation that the living being is moving since the water contained in vivo is frozen.

An electron beam is irradiated in order to perform electron microscopic observation, but it is required to acquire an electron microscopic image of a biological sample in the living state as it is without bringing about the deformation and/or degeneration of the biological sample by an electrical factor or thermal factor caused by this electron beam irradiation.

With regard to barrier performance, a technique, in which a film is formed on the surface of a sample by a means of spin coating, vapor deposition, coating, or the like using an organic material, an inorganic material, or an organic/inorganic hybrid material, thereby imparting barrier performance to the sample, has been suggested. However, there has been no example applying this barrier performance to the sample preparation for electron microscope so far.

The invention is made in view of the circumstances described above, and an object thereof is to provide an electron microscopic observation method capable of not deforming a sample and of suppressing damage of the state of a sample itself even under vacuum, and a composition for evaporation suppression under vacuum, a scanning electron microscope, and a transmission electron microscope used in the method.

In addition, another object of the invention is to provide an electron microscopic observation method capable of observing a biological sample as it is alive and a situation that the biological sample is moving using an electron microscope, and a composition for evaporation suppression under vacuum, a scanning electron microscope, and a transmission electron microscope used in the method.

Solution to Problem

In order to solve the problems described above, the sample observation method by an electron microscope of the invention includes applying a composition for evaporation suppression including at least one kind selected from an amphiphilic compound, oils and fats, and an ionic liquid to a surface of a sample to form a thin film and covering the sample with the thin film, and displaying an electron microscopic image of the sample, which is covered with the thin film and accommodated in a sample chamber under vacuum, on a display device.

In addition, the sample observation method by an electron microscope of the invention includes applying a composition for evaporation suppression containing at least one kind selected from an amphiphilic compound, oils and fats, and an ionic liquid to a surface of a sample, irradiating the sample applied with the composition for evaporation suppression with an electron beam or plasma to form a polymerized film on the surface of the sample as a thin film and covering the sample with the polymerized film, and displaying an electron microscopic image of the sample, which is covered with the polymerized film and accommodated in a sample chamber under vacuum, on a display device.

In a preferred aspect of this sample observation method by an electron microscope, the polymerized film is formed on a surface of a sample as a thin film by a polymerization reaction by irradiating the sample with an electron beam for sample observation in the sample chamber of an electron microscope. In another preferred aspect of this sample observation method by an electron microscope, the polymerized film is formed on a surface of a sample as a thin film by a polymerization reaction by irradiating the sample with an electron beam or plasma other than the electron beam for sample observation in advance before sample observation by electron microscope.

In still another preferred aspect of this sample observation method by an electron microscope, the composition for evaporation suppression includes at least one kind selected from an amphiphilic compound, a metal compound, and a saccharide.

In yet another preferred aspect of this sample observation method by an electron microscope, an electron microscopic image of a hydrated sample in a wet state is displayed on the displaying device without accompanying collapse of the hydrated sample.

In a still yet preferred aspect of this sample observation method by an electron microscope, the sample observation method includes applying a composition for evaporation suppression to a body surface of a living biological sample to form a thin film, and covering the sample with the thin film, and displaying an electron microscopic image of movement of the biological sample, which is covered with the thin film and accommodated in a sample chamber under vacuum, as it is alive on a display device. In this case, in a preferred aspect, the biological sample is provided with motility by suppressing decrease in temperature associated with evaporation from the inside of the biological sample body, and the morphology of the biological sample is preserved as it is, by the thin film. In another preferred aspect, wherein an internal body temperature of the biological sample, which enables the biological sample to be active, is maintained even under vacuum by the thin film.

In further another preferred aspect of this sample observation method by an electron microscope, an electron microscopic image of a sample is displayed on a display device without causing charging up of the sample using a scanning electron microscope.

The composition for evaporation suppression under vacuum of the invention is a composition for evaporation suppression under vacuum, which is used to form a thin film on a surface of a sample including an evaporable substance under vacuum and cover the sample, and thus to impart barrier performance suppressing evaporation of the evaporable substance under vacuum to the evaporable substance, and which includes at least one selected from an amphiphilic compound, oils and fats, and an ionic liquid.

In a preferred aspect of this composition for evaporation suppression under vacuum, the composition for evaporation suppression under vacuum is used to form a thin film on the body surface of a living biological sample and cover the biological sample, and thus to impart barrier performance suppressing evaporation of an evaporable substance under vacuum to the evaporable substance in the biological sample body.

In another preferred aspect of this composition for evaporation suppression under vacuum, a polymerized film is formed on a surface of a sample as a thin film by irradiating the sample applied with the composition for evaporation suppression with an electron beam or plasma, and the sample is covered with the polymerized film.

In still another preferred aspect of this composition for evaporation suppression under vacuum, the composition for evaporation suppression under vacuum includes at least one selected from an amphiphilic compound, a metal compound, and a saccharide.

The scanning electron microscope of the invention is a scanning electron microscope, which is used in the sample observation method by an electron microscope and includes a preliminary exhaust chamber capable of being introduced with a sample to be mounted in a sample chamber in the microscope body, and an exhauster deaerating the sample chamber and the preliminary exhaust chamber.

In a preferred aspect of the scanning electron microscope, the preliminary exhaust chamber is equipped with a glove box.

In another preferred aspect of the scanning electron microscope, the sample chamber or the preliminary exhaust chamber is equipped with a plasma irradiation device or an electron beam irradiation device.

In still another preferred aspect of the scanning electron microscope, the sample chamber or the preliminary exhaust chamber is equipped with a three dimensional manipulator capable of operating on a sample.

The scanning electron microscope of the invention is a scanning electron microscope, which is used in the sample observation method by an electron microscope, and includes a sample chamber equipped with a detection position regulatory mechanism capable of three dimensionally regulating a relative position of a secondary electron detector and a sample.

The scanning electron microscope of the invention is a scanning electron microscope, which is used in the sample observation method by an electron microscope, and includes a sample chamber equipped with a high speed color camera capable of acquiring color information of a sample.

The scanning electron microscope of the invention is a scanning electron microscope, which is used in the sample observation method by an electron microscope and includes a temperature regulator capable of regulating a temperature of a sample stub in a sample chamber.

The scanning electron microscope of the invention is a scanning electron microscope, which is used in the sample observation method by an electron microscope and includes a sample chamber equipped with at least one sensor selected from an electrical sensor, a light sensor, a gas sensor, a water sensor, and a temperature sensor.

The transmission electron microscope of the invention is a transmission electron microscope, which is used in the sample observation method by an electron microscope and includes a preliminary exhaust chamber capable of being introduced with a sample to be mounted in a sample chamber in the microscope body, and an exhauster deaerating the sample chamber and the preliminary exhaust chamber.

In a preferred aspect of this transmission electron microscope, the preliminary exhaust chamber is equipped with a glove box.

The transmission electron microscope of the invention is a transmission electron microscope used in the sample observation method by an electron microscope, in which each of the both sides of a grid mesh to be mounted with a sample has a polymerized film formed by irradiating the composition for evaporation suppression with an electron beam or plasma.

Advantageous Effects of Invention

According to the invention, it is possible to observe a sample at a high magnification without deforming the sample and without damaging the state of the sample itself.

In addition, it is possible to observe a living biological sample as it is alive and the ultrastructure of the living biological sample in a moving state using an electron microscope.

DESCRIPTION OF EMBODIMENTS

Figure 1:
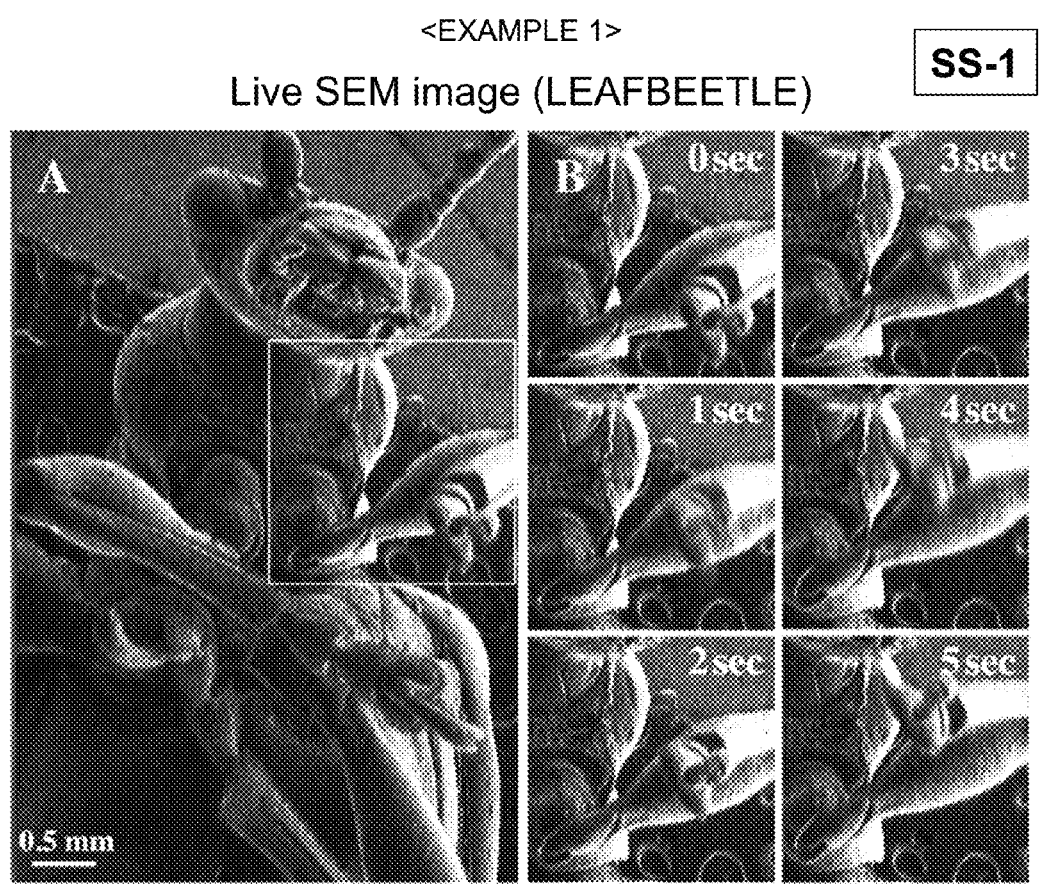
FIG. 1 is a photograph illustrating the situation of SEM video of Example 1.

Hereinafter, the invention will be described in detail.

The term "vacuum" in the invention means, for example, a range of $10^{-1}$ Pa or less, in addition $10^{-2}$ Pa to $10^{-4}$ Pa, and particularly $10^{-4}$ Pa to $10^{-8}$ Pa.

The composition for evaporation suppression of the invention forms a barrier on the surface of a biological sample to provide electron microscopic observation, in which the biological sample is introduced in the microscope body of an electron microscope in the living state as it is and observed in the living state as it is.

This barrier has a function (water barrier performance), by which the water in the living being is not dried but preserved in a liquid state as it is even under vacuum, and a function (gas barrier performance), by which the deaeration of gaseous substances such as oxygen in vivo is suppressed. In addition to these water/gas barrier performance, this barrier has a function (electrical conductivity/heat resistance), by which electrical and thermal deformation ad transformation caused by an electron beam irradiated to acquire an electron microscopic image, as well.

When a biological sample or a non-biological sample is observed using a current optical apparatus or electron beam apparatus, the observation is generally performed under a high vacuum condition, but under this condition, the sample is in a quite different state from the state under atmospheric pressure. The water and gaseous molecules in the sample cannot be preserved as in the state under atmospheric pressure, and thus the sample is significantly damaged in some cases. It is desired that observation is performed at a higher magnification while preserving a sample in its original shape as it is. In other words, it is desired that a dynamic observation is possible in real time without damaging the living state of a biological sample as it is in a case of a biological sample, and observation is possible without damage such as drying of a hydrated sample even in a case of a non-biological sample.

The inventors found that an amphiphilic compound, oils and fats, and an ionic liquid retains (has a water/gas barrier function) water and air (gas) under vacuum. A uniform protective film is formed by pouring this liquid on a biological sample, and thus water/gas barrier performance under atmospheric pressure and vacuum is exerted.

Particularly, when this liquid was employed for the observation of a biological sample using an electron microscope, it was possible to acquire a SEM image of a situation that a biological sample is moving since the biological sample was not dried in the microscope body of an electron microscope, was not accompanied with deformation and transformation, and was preserved in the living state as it is. Even at high magnification, there was no deformation or degeneration caused by an electron beam as well, and thus it was possible to observe a situation that a biological sample is moving. In addition, a favorable SEM observation was possible since charge up did not occur as well.

Water in vivo is not frozen since the biological sample is alive as it is even though the sample is put under vacuum. In other words, the observation result indicates that decrease in temperature associated with decompression is suppressed as well. This fact is confirmed by an experiment, in which the temperature of an amphiphilic compound is measured individually, the temperature of a combination of an amphiphilic compound and a metal compound or a saccharide is measured, the temperature of fats and oils is measured individually, or the temperature of an ionic liquid is measured individually under vacuum.

From this result, it is verified that an amphiphilic compound, a combination of an amphiphilic compound and a metal compound or a saccharide, fats and oils, or an ionic liquid are forms a protective film imparting a water/gas barrier performance. The inventors advance this water/gas barrier performance as the Surface Shielding Effect (SS effect).

An amphiphilic compound, a combination of an amphiphilic compound and a metal compound or a saccharide, fats and oils, or an ionic liquid imparts the Surface Shielding Effect (SS effect), and it is also found out that a protective film formed of these materials functions as a multifunctional barrier film since electrical conductivity is imparted and thermal damage caused by an electron beam is suppressed in addition to these barrier performances.

According to the invention, it is possible to observe a biological/living body sample in the living state as it is using an electron microscope. The invention provides not only a solution for electron microscopic observation of a biological/living body sample but also a constitution of the SS solution imparting the Surface Shielding Effect (SS effect) widely.

According to the invention, the SS solution imparting the Surface Shielding Effect (SS effect) contains an amphiphilic compound, contains an amphiphilic compound of a main component and a metal compound or a saccharide, contains fats and oils, or contains an ionic liquid, but the following items such as an amino acid and a derivative thereof, a vitamin and a derivative thereof, an inorganic salt, a metal oxide, and a fatty add and a derivative thereof, a conductive polymer, and a nanoclay can be added to the SS solution at an arbitrary proportion, and then the resultant SS solution can be used in various applications.

According to an aspect of the invention, the SS solution contains an amphipilic compound as a main component (base material). As the amphiphilic compound, for example, a surfactant can be used. Surfactants are roughly classified into an anionic surfactant, a cationic surfactant, a nonionic surfactant, a zwitterionic surfactant, and a naturally derived surfactant, and the like according to the molecular structure thereof. Surfactants are used in a variety of fields such as industry, food, and medical supplies, and the barrier performance can be basically exerted to a certain extent although any kinds of surfactants are used.

Among the surfactants described above, the anionic surfactant is classified into, for example, a carboxylic acid type, a sulfuric acid ester type, a sulfonic acid type, and a phosphoric acid ester type. Among these, specific examples thereof may include sodium dodecyl sulfate, sodium laurate, α-sulfofatty acid methyl ester sodium salt, sodium dodecylbenzenesulfonate, and sodium dodecylethoxylate sulfate. Among them, sodium dodecylbenzenesulfonate is preferably used.

Among the surfactants described above, the cationic surfactant is classified into, for example, a quaternary ammonium salt type, an alkyl amine type, and a heterocyclic amine type. Specific examples thereof may include stearyl trimethyl ammonium chloride, distearyl dimethyl ammonium chloride, didecyl dimethyl ammonium chloride, cetyl trimethyl pyridinium chloride, and dodecyl dimethyl benzyl ammonium chloride.

Among the surfactants described above, examples of the nonionic surfactant may include polyoxyethylene alkyl ether, polyoxyethylene hydrogenated castor oil, a polyoxyethylene mono-fatty acid ester, a polyoxyethylene sorbitan mono-fatty acid ester, a sucrose fatty acid ester, a polyglycerol fatty acid ester, an alkylpolyglycoside, and a N-methylalkylglucamide. Among them, commercially available products such as Triton™ X (Triton™ X-100 and the like), Pluronic® (Pluronic® F-123, F-68, and the like), Tween (Tween 20, 40, 60, 65, 80, 85, and the like), Brij® (Brij® 35, 58, 98, and the like), and Span (Span 20, 40, 60, 80, 83, and 85) are preferable in addition to dodecyl alcohol ethoxylate, nonylphenol ethoxylate, and lauroyl diethanolamide.

Among the surfactants described above, examples of the zwitterionic surfactant may include lauryl betaine, dodecyl dimethyl amino methyl sulfopropyl betaine, and 3-(tetradecyl dimethyl amino)propane-1-sulfonate, and 3-[(3-cholamidopropyl)dimethylammonio]-1-propanesulfonate (CHAPS), 3-[(3-cholamidopropyl)dimethylammonio]-2-hydroxy-1-propanesulfonate (CHAPSO), and the like are preferably used.

Among the surfactants described above, as the naturally derived surfactant, for example, lecithin and saponin are preferable. Among the compounds termed as lecithin, specifically phosphatidylcholine, phosphatidylethanolamine, phosphatidylinositol, phosphatidylserine, phosphatidic acid, phosphatidylglycerol, and the like are preferable. In addition, as saponin, Quillaja saponin is preferable.

Among the surfactants described above, as an amphiphilic compound derived from microorganisms (biosurfactant), Rhamnolipid, Sophorolipids, mannosylerythritol lipids, and the like are preferably used.

Among the surfactants generally used as a publicly known surfactant other than the surfactants exemplified above, examples of a surfactant, which is particularly used for cosmetics, may include almond oil PEG-6, Na acyl(C12, 14) aspartate, TEA acyl(C12, 14) aspartate, arachideth-20, stearyl alcohol, sodium alkyl(C11, 13, 15) sulfate, TEA alkyl(C11, 13, 15) sulfate, potassium alky(C11, 13, 15) phosphate, DEA alkyl(C12, 13) sulfate, sodium alkyl(C12, 13) sulfate, TEA alkyl(C12, 13) sulfate, alkyl(C12, 14, 16) ammonium sulfate, alkyl(C12-14) oxyhydroxypropyl arginine hydrochloride, alkyl(C12-14) diamino ethyl glycine hydrochloride, TEA alkyl(C12-14) sulfate, TEA alkyl(C12-15) sulfate, sodium alkyl(C14-18) sulfonate, alkyl(C16, 18) trimonium chloride, alkyl(C28) trimonium chloride, isostearamide DEA, isostearyl alcohol, isostearyl glyceryl, isostearyl lauryldimonium chloride, PEG-2 isostearate, PEG-3 isostearate, PEG-4 isostearate, PEG-6 isostearate, PEG-8 isostearate, PEG-10 isostearate, PEG-12 isostearate, PEG-15 glyceryl isostearate, PEG-20 isostearate, PEG-20 glyceryl isostearate, PEG-20 hydrogenated castor oil isostearate, PEG-20 sorbitan isostearate, PEG-30 isostearate, PEG-30 glyceryl isostearate, PEG-40 isostearate, PEG-50 hydrogenated castor oil isostearate, PEG-58 hydrogenated castor oil isostearate, PEG-60 glyceryl isostearate, PG isostearate, sorbitan isostearate, sorbeth-3 isostearate, polyglyceryl-2 isostearate, polyglyceryl-3 isostearate, polyglyceryl-4 isostearate, polyglyceryl-5 isostearate, polyglyceryl-6 isostearate, polyglyceryl-10 isostearate, isosteareth-2, isosteareth-10, Isosteareth-15, isosteareth-22, isostearoyl hydrolyzed collagen, AMPD-isostearoyl hydrolyzed collagen, isostearoyl sodium lactate, isoceteth-10, isoceteth-20, octyl isopalmitate, polyglyceryl-2 isopalmitate, sucrose acetate isobutyrate, potassium undecylenoyl hydrolyzed collagen, ethylenediaminetetrakis hydroxyisopropyl dioleate, epoxy ester-1, epoxy ester-2, epoxy ester-3, epoxy ester-4, epoxy ester-5, glyceryl erucate, PEG-4 octanoate, nonoxynol-14, octyldodeceth-2, octyldodeceth-5, octyldodeceth-10, octyldodeceth-30, TEA dextrin octenylsuccinate, octoxynol-1, sodium octoxynol-2 ethane sulfonate, octoxynol-10, octoxynol-25, octoxynol-70, olive oil PEG-6, PEG-3-PPG-20 oligosuccinate, oleamine oxide, oleyl betaine, oleyl sulfate, sodium oleyl sulfate, TEA oleyl sulfate, PEG-2 oleate, PEG-10 oleate, PEG-10 glyceryl oleate, PEG-15 glyceryl oleate, PEG-20 glyceryl oleate, PEG-30 glyceryl oleate, PEG-36 oleate, PEG-40 sorbitol oleate, PEG-75 oleate, PEG-150 oleate, PG oleate, sucrose oleate, hydroxy{bis(hydroxyethyl)amino}propyl oleate, polyglyceryl-2 oleate, polyglyceryl-5 oleate, polyglyceryl-10 oleate, oleoyl hydrolyzed collagen, oleoyl sarcosine, sodium oleoylmethyltaurinate, oleth-2, DEA oleth-3 phosphate, sodium oleth-7 phosphate, sodium oleth-8 phosphate, oleth-10, oleth-10 phosphoric acid, DEA oleth-10 phosphate, oleth-20, oleth-20 phosphate, oleth-30, oleth-50, sodium olefin (C14-16) sulfonate, cationized hydrolyzed wheat protein-1, cationized hydrolyzed wheat protein-3, cationized hydrolyzed conchiolin-2, cationized hydrolyzed soy protein-1, cationized hydrolyzed soy protein-2, cationized hydrolyzed soy protein-3, cationized dextran-2, capramide DEA, glyceryl ester of beef tallow fatty acid, apricot kernel oil PEG-6, distearyl citrate, glyceryl ester of citric acid and fatty acid, quaternium-14, quaternium-18, quaternium-18 hectorite, quaternium-18 bentonite, quaternium-22, quaternium-33, corn oil PEG-6, corn oil PEG-8, cocamide, disodium cocamide DEA, cocamide MEA, cocamidopropyl betaine, cocoamine oxide, sodium cocoamphoacetate, disodium cocoamphodiacetate, sodium polyoxyethylene tridecyl sulfate, disodium cocoamphodipropionate, sodium cocamphopropionate, cocoyl alanine TEA, PCA ethyl cocoyl arginate, sodium cocoyl isethionate, potassium cocoyl hydrolyzed casein, potassium cocoyl hydrolyzed keratin, potassium cocoyl hydrolyzed yeast, potassium cocoyl hydrolyzed yeast protein, potassium cocoyl hydrolyzed wheat protein, cocoyl hydrolyzed collagen, potassium cocoyl hydrolysis collagen, sodium cocoyl hydrolyzed collagen, TEA cocoyl hydrolyzed collagen, potassium cocoyl hydrolyzed potato protein, potassium cocoyl hydrolyzed soy protein, potassium cocoyl hydrolyzed corn protein, potassium cocoyl hydrolyzed potato protein, potassium cocoyl glycine, TEA cocoyl glycine, cocoyl glutamic acid, potassium cocoyl glutamate, sodium cocoyl glutamate, TEA cocoyl glutamate, cocoyl sarcosine, sodium cocoyl sarcosinate, TEA cocoyl sarcosinate, sodium cocoyl taurate, cocoyl methyl alanine, sodium cocoyl methyl alanine, potassium cocoyl methyl taurate, magnesium cocoyl methyl taurate, sodium cocoyl methyl taurate, sodium coco glyceryl sulfate, cocodimonium hydroxypropyl hydrolyzed keratin, cocodimonium hydroxypropyl hydrolyzed collagen, cocodimonium hydroxypropyl hydrolyzed silk, coco betaine, PEG-50 hydrogenated castor oil succinate, glyceryl ester of succinic acid and fatty acid, choleth-10, choleth-15, isoceteth-3 acetate, ceteth-3 acetate, isobutyl acetate, ethyl acetate, glyceryl acetate, glyceryl ester of acetic acid and fatty acid, sucrose acetate stearate, trideceth-3 acetate, trideceth-15 acetate, butyl acetate, glyceryl monostearate, Laneth-9 acetate, glyceryl fatty acid diacetyl tartrate, dialkyl(C12-15) dimonium chloride, dialkyl(C12-18) dimonium chloride, PEG-8 isostearate, PG diisostearate, diisostearate-2, PEG-4 dioleate, PEG-10 dioleate, PEG-32 dioleate, PEG-75 dioleate, PEG-120 methyl glucose dioleate, PEG-150 dioleate, PG dioleate, glycol dioleate, polyglyceryl-6 dioleate, cellulose di(beef tallow alkyl) dimolynium sulfate, dicoco dimolynium chloride, glyceryl diacetate stearate, distearyl dimolynium chloride, PEG-2 distearate, PEG-12 distearate, PEG-20 methyl glucose distearate, PEG-120 distearate, PEG-250 distearate, PEG-trimethylolpropane distearate, PG distearate, PPG-20 methyl glucose distearate, glycol distearate, glyceryl distearate, sucrose distearate, sorbitan distearate, polyglyceryl-6 distearate, polyglyceryl-10 distearate, dicetyldimonium chloride, MEA dicetearyl phosphate, dihydroxy ethyl stearyl betaine, PEG-3 dipalmitate, dihydroxy ethyl lauramine oxide, (dihydroxy methyl silyl propoxy) hydroxypropyl hydrolyzed casein, (dihydroxy methyl silyl propoxy) hydroxypropyl hydrolyzed collagen, (dihydroxy methyl silyl propoxy) hydroxypropyl hydrolyzed silk, dihydrocholeth-15, (C8-22) polyglyceryl-10 ester of fatty acid, dimethicone copolyol, dimethicone copolyol acetate, dimethicone copolyol butyl, dimethyl stearamine, PEG-4 dilaurate, PEG-12 dilaurate, PEG-32 dilaurate, sucrose dilaurate, dilaureth-4 phosphate, dilaureth-10 phosphate, magnesium dilauroyl glutamate, lecithin hydroxide, hydrogenated cocoglyceryl, glyceryl ester of hydrogenated soybean fatty acid, hydrogenated tallow amide DEA, disodium hydrogenated tallow glutamate, TEA hydrogenated tallow glutamate, hydrogenated lanolin, hydrogenated lanolin alcohol, hydrogenated lysolecithin, hydrogenated lecithin, stearamide, stearamide DEA, stearamide MEA, stearamidopropyl diethylamine, stearamidopropyl dimethylamine, stearamine oxide, stearalkonium chloride, stearalkonium hectorite, sodium stearyl dimethyl betaine, stearyl trimonium saccharin, stearyl trimonium bromide, stearyl betaine, sodium stearyl sulfate, PEG-2 stearate, PEG-6 sorbitol stearate, PEG-10 stearate, PEG-10 glyceryl stearate, PEG-14 stearate, PEG-20 glyceryl stearate, PEG-23 stearate, PEG-25 stearate, PEG-40 stearate, PEG-100 stearate, PEG-120 glyceryl stearate, PEG-150 stearate, PEG-200 glyceryl stearate, PG stearate, TEA stearate, glycol stearate, glyceryl stearate, sucrose stearate, steareth-4 stearate, stearoyl dihydroxy isobutylamide stearate, sorbitan stearate, polyoxyethylene cetyl ether stearate, polyglyceryl-2 stearate, polyglyceryl-10 stearate, glyceryl stearate/malate, steardimonium hydroxydipropyl hydrolyzed keratin, steardimonium hydroxydipropyl hydrolyzed collagen, steardimonium hydroxydipropyl hydrolyzed silk, steartrimonium chloride, steareth-2 phosphate, steareth-3, steareth-10, steareth-16, steareth-50, steareth-80, steareth-100, potassium stearoyl hydrolyzed collagen, sodium stearoyl hydrolyzed collagen, stearoyl glutamate, disodium stearoyl glutamate, potassium stearoyl glutamate, sodium stearoyl glutamate, dioctyldodecyl stearoyl glutamate, stearoyl colamino formyl methyl pyridinium chloride, calcium stearoyl lactylate, sodium stearoyl lactylate, sodium stearoyl methyl taurate, disodium (C12-14) pareth sulfosuccinate, disodium PEG-2 oleamide sulfosuccinate, disodium PEG-4 cocoyl isopropanolamide sulfosuccinate, disodium PEG-5 lauramide sulfosuccinate, sodium dioctyl sulfosuccinate, sodium sitostereth-14-2 sulfosuccinate, disodium lauryl sulfosuccinate, disodium laureth sulfosuccinate, sorbitan sesquiisostearate, glyceryl sesquioleate, sorbitan sesquioleate, diglyceryl sesquioleate, PEG-20 methyl glucose sesquistearate, sorbitan sesquistearate, methyl glucose sesquistearate, cetyl dimethicone copolyol, cetyl pyridinium chloride, sodium cetyl sulfate, DEA cetyl phosphate, potassium cetyl phosphate, cetearyl alcohol, cetearyl glucoside-cetearyl alcohol, sodium cetearyl sulfate, ceteareth-10, ceteareth-15, ceteareth-22, ceteareth-34, ceteareth-55, ceteareth-60, ceteareth-60 myristyl glycol, ceteareth-100, ceteth-8 phosphate, ceteth-10, ceteth-10 phosphate, ceteth-12, ceteth-24, ceteth-45, cetrimonium chloride, cetrimonium saccharin, cetrimonium bromide, cetoleth-10, cetoleth-20, cetoleth-25, tallow amide MEA, polyglyceryl-10 decaisostearate, polyglyceryl-10 decaoleate, polyglyceryl-10 decastearate, decyl glucoside, diglycerol sorbitan tetraoctanate, sorbeth-30 tetraoleate, sorbeth-40 tetraoleate, sorbeth-60 tetraoleate, sorbeth-60 tetrastearate, TEA dodecyl benzene sulfonate, tri-PEG-8 alkyl (C12-15) phosphate, tri(PEG-3 isostearate) trimethylolpropane, PEG-10 glyceryl triisostearate, PEG-15 hydrogenated castor oil triisostearate, PEG-20 hydrogenated castor oil triisostearate, PEG-30 glyceryl triisostearate, PEG-30 hydrogenated castor oil triisostearate, PEG-50 glyceryl triisostearate, PEG-50 hydrogenated castor oil triisostearate, PEG-160 sorbitan triisostearate, polyglyceryl-2 triisostearate, sorbitan trioleate, polyglyceryl-10 trioleate, PEG-3 sorbitol tristearate, PEG-140 glyceryl tristearate, PEG-160 sorbitan tristearate, sucrose tristearate, sorbitan tristearate, polyglyceryl-10 tristearate, trideceth-sodium triacetate, trideceth-sodium hexaacetate, trideceth-9, trideceth-10, trideceth-11, trideceth-20, trideceth-21, trihydroxystearin, sucrose tribehenate, trilaurylamine, tri laureth-tetraphsphate, tri laureth-sodium tetraphosphate, glyceryl fatty acid lactylate, nonyl nonoxynol-10, nonyl nonoxynol-100, nonoxynol-3, sodium nonoxynol-4 sulfate, nonoxynol-6 phosphate, nonoxynol-6 sodium phosphate, nonoxynol-10, nonoxynol-10 phosphate, nonoxynol-23, nonoxynol-50, nonoxynol-120, perfluoroalkyl PEG phosphate, DEA perfluoroalkyl phosphate, palm kernel fatty acid amide DEA, sodium palm kernel fatty acid amide ethyl hydroxyethyl aminopropionate, palm kernel fatty acid amide propyl betaine, sodium palm fatty acid glutamate, palmitamide MEA, PEG-6 palmitate, PEG-18 palmitate, PEG-20 palmitate, sucrose palmitate, sorbitan palmitate, di-TEA palmitoyl aspartate, sodium palmitoyl methyl taurate, peanut oil PEG-6, glyceryl hydroxy steaate, hydroxypropyltrimonium hydrolyzed casein, hydroxypropyltrimonium hydrolyzed keratin, hydroxypropyltrimonium hydrolyzed wheat protein, hydroxypropyltrimonium hydrolyzed collagen, hydroxypropyltrimonium hydrolyzed silk, hydroxy lanolin, PPG-2 myristyl propionate, polyglyceryl-10 heptastearate, heptadecyl hydroxyethyl carboxylate methyl imidazolium, behenamidopropyl PG-dimonium chloride, behenamine oxide, beheneth-10, beheneth-30, glyceryl behenate, behentorimonium chloride, benzalkonium chloride, polyglyceryl-10 pentaisostearate, diglycerol sorbitan pentaoctanate, PEG-40 sorbitol pentaoleate, polyglyceryl-6 pentaoleate, polyglyceryl-10 pentaoleate, polyglyceryl-10 pentastearate, potassium polyacrylate, sodium polyacrylate, ammonium polyacrylate, TEA polyoxyethylene alkyl phenyl ether phosphate, sodium polyoxyethylene ether phosphate, polyoxyethylene octyl ether phosphate, polyoxyethylene cetyl stearyl diether, polyoxyethylene phytostanol, polyoxyethylene butyl ether, polyoxyethylene coconut fatty acid diethanolamide, TEA polyoxyethylene lauryl ether phosphate, polyoxypropylene carboxy alkyl(C14-18) diglucoside, polyoxypropylene glyceryl ether phosphate, polyoxypropylene sorbit, sucrose polyoleate, polyglyceryl-2 oleyl, sucrose polystearate, cetyl acetate, acetylated lanolin alcohol, sucrose palm fatty acid polyester, sucrose polylaurate, polyglyceryl polyricinoleate, sucrose polylinoleate, Poloxamer 181, Poloxamer 333, Poloxamine 304, Poloxamine 901, Poloxamine 1104, Poloxamine 1302, Poloxamine 1508, (C12, 14) hydroxyalkyl maltitol, miristamide DEA, myristamin oxide, myristal konium chloride, myristyl PG hydroxyethyl decanamide, myristyl betaine, sodium myristyl sulfate, PEG-8 myristate, PEG-20 myristate, glyceryl myristate, sucrose myristate, polyglyceryl-10 myristate, myreth-3 myristate, myristoyl hydrolyzed collagen, potassium myristoyl hydrolyzed collagen, myristoyl glutamate, potassium myristoyl glutamate, sodium myristoyl glutamate, sodium myristoyl sarcosinate, sodium myristoyl methyl alanine, sodium myristoyl methyl taurate, myreth-3, sodium myreth-3 sulfate, glyceryl monoacetate monostearate, TEA of coconut fatty acid, glyceryl ester of coconut fatty acid, sucrose ester of palm fatty acid, sorbitan ester of coconut fatty acid, lysine ester of coconut fatty acid, lauramide DEA, lauramide MEA, lauramide propyl betain, sodium lauraminodiacetate, lauraminopropionic acid, sodium lauraminopropionate, lauramine oxide, sodium lauraminodipropionate, lauryl DEA, lauryl isoquinolinium saccharin, lauryl isoquinolinium bromide, lauryl glucoside, sodium lauryl diaminoethyl glycine, lauryl dimonium hydroxypropyl hydrolyzed keratin, lauryl dimonium hydroxypropyl hydrolyzed collagen, lauryl dimonium hydroxypropyl hydrolyzed silk, sodium lauryl sulfonate, lauryl hydroxy acetate amide sulfate, lauryl hydroxysultaine, lauryl pyridinium chloride lauryl betaine, DEA lauryl sulfate, potassium lauryl sulfate, MEA lauryl sulfate, magnesium lauryl sulfate, sodium lauryl sulfate, TEA lauryl sulfate, ammonium lauryl sulfate, lauryl phosphoric acid, disodium lauryl phosphate, sodium lauryl phosphate, PEG-2 laurate, PEG-4 DEA laurate, PEG-6 laurate, PEG-8 laurate, PEG-8 glyceryl laurate, PEG-9 laurate, PEG-10 laurate, PEG-12 glyceryl laurate, PEG-23 glyceryl laurate, PEG-32 laurate, PEG-75 laurate, PEG-150 laurate, PEG sorbitol laurate, PG laurate, TEA laurate, glyceryl laurate, sucrose laurate, polyoxyethylene hydrogenated castor oil laurate, polyglyceryl-6 laurate, polyglyceryl-10 laurate, maltitol laurate, lauryl trimonium chloride, lauryl trimonium bromide, ammonium laureth-2 sulfate, laureth-3 acetate, TEA laureth-3 sulfate, ammonium laureth-3 sulfate, laureth-3 phosphate, laureth-4 phosphate, sodium laureth-4 phosphate, potassium laureth-4.5 acetate, laureth-5 acetate, sodium laureth-5 laureth-6 acetate, sodium laureth-6 acetate, laureth-7 phosphate, laureth-9, laureth-10, laureth-10 acetate, potassium laureth-10 acetate, sodium laureth-16 acetate, sodium laureth-17 acetate, laureth-40, TEA laureth sulfate, sodium lauroampho PG-acetate phosphate, sodium lauroampho acetate, lauroyl aspartic acid, potassium lauroyl hydrolyzed collagen, sodium lauroyl hydrolyzed collagen, sodium lauroyl hydrolyzed silk, lauroyl glutamic acid, potassium lauroyl glutamate, sodium lauroyl glutamate, TEA lauroyl glutamine glutamate, dioctyldodecyl lauroyl glutamate, dioctyl dodeceth-2 lauroyl glutamate, dioctyldodecyl lauroylglutamate, dicholesteryl lauroyl glutamate, disteareth-2 lauroyl glutamate, disteareth-5 lauroyl glutamate, lauroylsarcosine, sodium lauroyl sarcosinate, TEA lauroyl sarcosinate, potassium lauroyl threonate, sodium lauroyl lactylate, lauroyl methyl alanine, sodium lauroyl methyl alanine, TEA lauroyl methyl alanine, sodium lauroyl methyl taurate, laneth-10, laneth-25, laneth-40, laneth-75, PEG-4 ester of lanolin fatty acid, PEG-12 ester of lanolin fatty acid, DEA lanolin fatty acid amide, isopropyl ester of lanolin fatty acid, octyldodecyl ester of lanolin fatty acid, glyceryl of lanolin fatty acid, cholesteryl ester of lanolin fatty acid, Lapyrium chloride, amidopropyl betaine ricinoleate, glyceryl ricinoleate, sucrose ricinoleate, polyoxypropylene sorbit ricinoleate, polyglyceryl-6 ricinoleate, lanolin linoleate, linoleamide DEA, sulfated castor oil, malic acid lauramide, rosin hydrolyzed collagen, and AMPD-rosin hydrolyzed collagen.

A fluorosurfactant can also be used in addition to the surfactants described above. Specific examples of the fluorosurfactant may include ammonium heptadecafluoro-1-octanesulfonate, ammonium pentadecafluorooctanate, heptadecafluorooctanesulfonic acid, lithium heptadecafluoro-1-octanesulfonate, pentadecafluorooctanoic acid, pentadecafluorooctanoic acid hydrate, and potassium heptadecafluoro-1-octanesulfonate.

The following surfactants can also be used in addition to the surfactants described above. Examples thereof may include an anionic surfactant such as a N-long chain acyl amino acid salt such as a N-long chain neutral amino acid salt such as a N-long chain acyl glutamic acid salt, a N-long chain acyl aspartic add salt, a N-long chain acyl glycine salt, a N-long chain acyl alanine salt, a N-long chain acyl threonine salt, and a N-long chain acyl sarcosine salt, a N-long chain fatty acid acyl-N-methyl taurine salt, an alkyl sulfate and an alkylene oxide adduct thereof, a fatty acid amide ether sulfate, a metal salt of fatty acid, a sulfosuccinic acid-based surfactant, an alkyl phosphate and an alkylene oxide adduct thereof, a higher alkyl sulfate salt, an alkyl ether sulfate salt, an alkyl hydroxy ether carboxylate salt, and an alkyl ether carboxylic acid, a nonionic surfactant such as an ether type surfactant such as a glycerol ether and an alkylene oxide adduct thereof, a ester type surfactant such as a glycerin ester and an alkylene oxide adduct thereof, an ether ester type surfactant such as a sorbitan ester and an alkylene oxide adduct thereof, a fatty acid alkylolamide such as a fatty acid monoethanolamide and a fatty acid diethanolamide, an ester type surfactant such as a polyoxyalkylene fatty acid ester, a polyoxyalkylene polyhydric alcohol fatty acid ester, a polyoxyalkylene sorbitan fatty acid ester, a polyoxyalkylene hydrogenated castor oil, glyceryl monostearate, a glyceryl ester, a fatty acid polyglycerol ester, an acylamino acid polyglycerol ester, a sorbitan ester, an a sucrose fatty acid ester, and a nitrogen-containing type nonionic surfactant such as an alkylglucoside, a hydrogenated castor oil pyroglutamic acid diester and an ethylene oxide adduct thereof, a fatty acid alkanolamide, and a zwitterionic surfactant such as a cationic amphiphilic compound such as an alkylamine salt such as an alkyl ammonium chloride, a dialkyl ammonium chloride, an alkyl trimethyl ammonium chloride (C16-C22), and a dialkyl dimethyl ammonium methosulfate salt, an aromatic quaternary ammonium salt such as a quaternary ammonium salt of the alkylamine salt and a benzalkonium salt, a fatty acyl arginine ester, a N-long chain acyl arginine ethyl pyrrolidone carboxylate, amidoamine, stearamidopropyl dimethylamine glutamate, stearamidopropyl dimethylamine lactate, stearamidopropyl dimethylamine pyrrolidone carboxylate, behenamidopropyl dimethylamine glutamate, behenamidopropyl dimethylamine lactylate, and behenamidopropyl dimethylamine pyrrolidone carboxylate, a betaine type amphiphilic compound such as an alkyl betaine, a alkylamide betaine, sulfobetaine, imidazolinium betaine, amino propionate, and carboxybetaine, a N-long chain acyl arginine, N-(3-alkyl(12, 14) oxy-2-hydroxypropyl) arginine hydrochloride, an amino acid surfactant, and an imidazoline surfactant.

According to an aspect of the invention, the SS solution contains an amphiphilic compound and a metal compound. As the metal compound, a substance containing a metal ion can be widely used.

The metal compound may be a salt consisting of a cation and an anion (monosalt), or a salt consisting of two or more of cations and anions (double salt).

The metal compound may be a compound such as an oxide, a hydroxide, a halide, a sulfate salt, a nitrate salt, a carbonate salt, and an acetate salt. Specific examples thereof may include sodium chloride, magnesium chloride, calcium chloride, sodium bicarbonate, potassium chloride, strontium chloride, lithium chloride, hafnium chloride, iron chloride, aluminum chloride, zinc chloride, copper chloride, cobalt chloride, magnesium sulfate, and magnesium carbonate.

The metal compound may be a metal oxide. A metal alkoxide is a compound indicated by MOR, and consists of a metal (M) and an alkoxide (RO⁻) (R represents a hydrocarbon). Specific examples of metal (M) may include silicon, titanium, aluminum, boron, zirconium, boron, vanadium, tungsten, phosphorus, germanium, indium, hafnium, and molybdenum. A metal alkoxide is obtained from various kinds of alcohols. These metal alkoxides may be used as it is, or a reaction product obtained by performing a sol-gel reaction of these metal alkoxides in the presence of an acid or an alkali may be used. As the metal alkoxide, two or more kinds may be mixed together instead of using a single component.

The metal compound may be a metal complex.

According to another aspect of the invention, the SS solution contains an amphiphilic compound and a saccharide. With regard to the combination of a saccharide and an amphiphilic compound, imparting the SS effect is new finding by the inventors. As the saccharide, a monosaccharide, a disaccharide, an oligosaccharide, a polysaccharide, and a derivative thereof are blended. Examples of the monosaccharide may include glucose and fructose, and examples of the disaccharide may include sucrose. Examples of the polysaccharide may include heparin, chondroitin sulfate, pullulan, pectin, guar gum, xanan xanthan gum, carrageenan, propylene glycol, and carboxymethyl cellulose, and a polysaccharide such as pullulan is particularly preferable. In addition to the saccharides described above, caramel, honey, beeswax may be used.

In addition, according to still another aspect of the invention, the SS solution contains fats and oils.

As the fats and oils, silicon oil may be exemplified. Silicon oil functions as a water retaining agent preserving the aqueous environment of the tissue or cell of a biological sample, dynamic observation of the biological sample as it is alive is achieved by this function. In other words, silicon oil can be used as a material having a barrier performance, by which the water of tissue or cell is not lost even under vacuum.

As the silicon oil, for example, silicon oil having a viscosity of 1 to 100,000 mPa·s at 25° C. can be used. For example, "636-04001" manufactured by Wako Pure Chemical Industries, Ltd, "KF-54" and "KF-96" manufactured by Shin-Etsu Chemical Co., Ltd. and the like can be used.

The composition for evaporation suppression (SS solution) of the invention, which uses silicon oil, preferably contains the silicon oil 10% by weight or more with respect to the total amount of the composition, and the components exemplified below may be blended as a component other than the silicon oil.

In addition, according to yet another aspect of the invention, the SS solution contains an ionic liquid.

Examples of the ionic liquid may include imidazolium salts, pyridinium salts, piperidinium salts, pyrrolidinium salts, quaternary ammonium salts, phosphoniums, sulfoniums, and pyrazoliums.

Examples of the imidazolium salts may include 1-alkyl-3-alkylimidazolium, 1,3-dimethylimidazolium, 1-ethyl-3-methylimidazolium, 1-butyl-3-methylimidazolium, 1-hexyl-3-methylimidazolium, 3-methyl-1-octylimidazolium, 1-dodecyl-3-methylimidazolium, 1-dodecyl-3-methylimidazolium, 1-methyl-3-tetradecylimidazolium, 1-hexadecyl-3-imidazolium, 1-octadecyl-3-methylimidazolium, 1-allyl-3-methylimidazolium, 1 allyl 3 methylimidazolium, 1 allyl-3-ethylimidazolium, 1-allyl-3-butylimidazolium, 1,3-diallylimidazolium, 1-benzyl-3-methyl-imidazolium, and 1-(2-hydroxyethyl)-3-methylimidazolium.

Examples of the 1-alkyl-2,3-dialkylimidazolium salt may include 1-ethyl-2,3-dimethylimidazolium, 1,2,3-triethylimidazolium, 1,2-dimethyl-3-propylimidazolium, 1-butyl-2,3-dimethylimidazolium, 1-hexyl-2,3-dimethylimidazolium, and 1,3-dodecyl-2-methylimidazolium.

Examples of the pyridinium salts may include 1-methylpyridinium, 1-ethylpyridinium, 1-butylpyridinium, 1-hexylpyridinium, 1-ethyl-3-methylpyridinium, 1-methyl-4-methylpyridinium, 1-propyl-4-methylpyridinium, 1-propyl-3-methylpyridinium, 1-butyl-2-methylpyridinium, 1-butyl-3-methylpyridinium, 1 ethyl-3-hydroxymethylpyridinium, and 1-(3-hydroxypropyl)pyridinium.

Examples of the piperidinium salts may include 1-methyl-1-propylpiperidinium, 1-butyl-1-methylpiperidinium, and 1-(methoxyethyl)-1-methylpiperidinium.

Examples of the pyrrolidinium salts may include 1,1-dimethylpyrrolidinium, 1-ethyl-1-methylpyrrolidinium, 1-methyl-1-propylpyrrolidinium, 1-butyl-1-methylpyrrolidinium, and 1-(methoxyethyl)-1-methylpyrrolidinium.

Examples of the quaternary ammonium salts may include choline, N,N-diethyl-N-methyl-N-(2-methoxyethyl)ammonium, and trimethylamine oxide in addition to tetramethylammonium, tetrabutylammonium, butyltrimethylammonium, ethyl-dimethyl-propyl ammonium, tributylmethylammonium, methyltrioctylammonium, and 2 hydroxyethylammonium.

Examples of the phosphoniums may include tetrabutylphosphonium, tributylhexadecylphosphonium, triethylpentylphosphonium, triethyloctylphosphonium, tetraoctylphosphonium, tri-isobutylmethylphosphonium, tributyltetradecyiphosphonium, and triethyltetradecylphosphonium.

Examples of the sulfoniums may include triethylsulfonium and diethylmethylsulfonium.

Examples of the pyrazoliums may include guanidinium and N-(methoxyethyl)-N-methylmorpholinium in addition to 1-ethyl-2,3,5-trimethylpyrazolium, 1-propyl-2,3,5-trimethylpyrazolium, and 1-butyl-2,3,5-trimethylpyrazolium.

Among the above described compounds, which are termed as an ionic liquid, the anionic moiety may be the following ones. In other words, the anionic moiety may be, in addition to a saturated/unsaturated hydrocarbon group, an aromatic hydrocarbon group, an ether group, an alkyl hydroxyl group, chloride ion, bromide ion, iodide ion, acetate ion, lactate ion, methoxy sulfonate ion, ethoxy sulfonate ion, dimethoxy phosphate ion, n-butyl sulfonate ion, diethoxy phosphate ion, ethyl sulfonate ion, n-hexyl phosphate ion, hydrogen phosphate ion, thiocyanate ion, octyl sulfonate ion, 2-(2-methoxyethoxy)ethyl sulfate ion, tricyanomethane, tetrafluoroborate ion, hexafluorophosphate ion, triflate ion, bis(trifluoromethylsulfonyl)imide, trifluoromethanesulfonate ion, bis(fluoro sulfonyl)imide, bis(nonafluorobutanesulfonyl)imide, ethyl sulfate ion, perfluorobutane sulfonate ion, dicyanamide, trifluoroacetate ion, formate ion, dihydrogen phosphate ion, bicarbonate ion, methyl carbonate ion, dibutyl phosphate ion, tris(pentafluoroethyl) trifluorophosphate ion, bis [oxalate (2−)-O,O'] borate ion, decanoate ion, bis(2,4,4-trimethyl-pentyl) phosphinate ion, dodecylbenzene sulfonate ion, p-triene sulfonate ion, diethyl phosphonate ion, benzoate ion, thiosalicynate ion, tetrachloroferrate ion, tetrachloroaluminate ion, and hexafluoroantimonate ion.

In addition, the anionic moiety may be an arbitrary amino acid obtained by ion exchange through the method disclosed in J. Am. Chem. Soc., 2005, 127, 2398 to 2399. The amino acid descried herein may be a monomer, or a dipeptide or an oligopeptide. Moreover, a counter ion is in a proportion of 1:1 with respect to a imidazolium salt in Non Patent Literature 3, but the proportion of 1:1 is not required with regard to an ionic liquid in the invention.

In addition, according to the invention, the SS solution contains an amphiphilic compound, or contains an amphiphilic compound and a metal compound or contains a saccharide, or contains fats and oils, or contains an ionic liquid, and an amino acid exemplified in the following item and a derivative thereof, a polyhydric alcohol, a vitamin and a derivative thereof, a fatty acid and a derivative thereof, a polymeric material, and the like may be added at an arbitrary proportion in addition to these components.

As a component of the solution imparting the SS effect, an amino acid and a derivative thereof may be blended. Examples of the amino acid may include a simple substance such as glycine, alanine, valine, leucine, isoleucine, serine, threonine, cysteine, methionine, asparagine, glutamine, proline, phenylalanine, tyrosine, tryptophan, aspartic acid, glutamic acid, lysine, arginine, and histidine, a hydrochloride, a substance formed by bonding of two or more molecules, and a polymer thereof. These may be a single of one kind or a mixture of two or more kinds. Furthermore, these may be a derivative thereof.

As a component of the solution imparting the SS effect, a polyhydric alcohol and a derivative thereof may be blended. A substance having a hydroxyl group in the molecule and a low vapor pressure is preferable. Specific examples thereof may include a substance other than the naturally derived amphiphilic compounds, such as glycerin, a triglyceride, polyresorcinol, a polyphenol, tannic acid, and urushiol, and particularly, tannic acid is preferably used.

As a component of the solution imparting the SS effect, a vitamin and a derivative thereof, and a substance related thereto may be blended. Specific examples thereof may include vitamin $B_1$, vitamin $B_2$, vitamin $B_3$, vitamin $B_5$, vitamin $B_6$, vitamin $B_7$, vitamin $B_9$, vitamin $B_{12}$, vitamin A, vitamin D, vitamin E, and vitamin K, or a derivative thereof. Among them, retinal, β-carotene, vitamin $B_3$ (nicotinic acid, nicotinamide), vitamin $B_6$ (pyridoxine, pyridoxal, pyridoxamine), and vitamin $B_9$ (folic acid) are preferable. Furthermore, examples of the vitamin derivative may include D-araboascorbic acid, setflavin T, 4-deoxypyridoxine hydrochloride, dibenzoyl thiamine, 2,6-di-O-palmitoyl-L-ascorbic acid, flavin adenine dinucleotide disodium hydrate, (+)-5,6-O-isopropylidene-L-ascorbic acid, 6-O-palmitoyl-L-ascorbic acid, proflavin hemisulfate hydrate, pyridoxal hydrochloride, pyridoxal 5-phosphate monohydrate, pyridoxine 3,4-dipalmitate, sodium isoascorbate monohydrate, thiamine disulfide hydrate, and thiamine disulfide nitrate. Examples of the substance related to vitamin may include choline chloride, choline bromide, choline dihydrogen citrate, choline bitartrate coenzyme Q10, coenzyme Qo, methionine methylsulfonyl chloride, and inositols.

Examples of the polymeric material may include polyvinyl alcohol, Teflon (registered trademark), polyvinylidene fluoride, tetraethoxysilane, tetramethoxysilane, titanium isopropoxide, and zirconium butoxide.

As a component of the solution imparting the SS effect, the ionic liquids described above may be additionally blended with other essential components.

As a component of the solution imparting the SS effect, the following components may be blended in addition to the components exemplified above, such as an amphiphilic compound, a metal compound, a saccharide, and the like.

Coordination compound: crown ether, cyclodextrin, cyclic tetramer of resorcinol, calixarene, a dendrimer and the like.

Fatty acid and derivative thereof: linolic acid, oleic acid, palmitic acid, linoleic acid, and the like.

Derivative of saccharide and fatty acid: hyaluronic acid, ceramide, an amphiphilic compound, collagen, an amino acid, an essential oil, petrolatum, and the like.

Gelatinizer: poly(pyridinium-1,4-diyliminocarbonyl-1,4-phenylenemethylene chloride and the like.

Colorant: paprika pigment, malachite green, and the like in addition to chlorophyll, carotenoids (lycopene), phycobilin, melanin, and the like.

Conductive polymer: Nafion and the like in addition to polyacetylene, polyaniline, polythiophene, and the like.

Nanoclay: a commercially available product having a trade name of Nanoclay Nanomer® Laponite or montmorillonite and the like.

Matrix material used as a reagent for mass spectrometry, mainly in MALDI method: 3-amino-4-hydroxybenzoic acid, sinapic acid, esculetin, 4-hydroxy-azobenzene-2'-carboxylic acid, 3-hydroxy-2-pyridine carboxylic acid, nicotinic acid, 2',4',6'-trihydroxyacetophenone, α-cyano-4-hydroxycinnamic acid, 2,5 dihydroxybenzoic acid, and the like.

The composition for evaporation suppression of the invention may be in a solid state or in a liquid form, but is preferably a composition in a liquid form and highly viscous state in order to preserve the aqueous environment of the tissue of a sample under vacuum. In addition, a composition in a solid state can be changed into a liquid state and then used at the time of use.

The composition for evaporation suppression of the invention can be formed into a significantly thin film on the surface of a sample by, for example, dissolving the respective components described above in water, an organic solvent, or the like, and directly coating or the like on the sample.

In the composition for evaporation suppression of the invention, the blending proportion of the amphiphilic compound, and a metal compound and a saccharide is not particularly limited, and, for example, the following constitutions are exemplified as a preferred blending proportion.

(1) Amphiphilic compound (sodium dodecylbenzenesulfonate)/metal compound (ethylenediamine nickel complex)=0.005/0.001 to 0.05/0.01

(2) Amphiphilic compound (sodium dodecyl sulfate)/metal compound (ethylenediamine nickel complex)=0.005/0.0001 to 0.05/0.001

(3) Amphiphilic compound (sodium dodecylbenzenesulfonate)/metal compound (tetraamine cobalt complex)=0.00510.001 to 0.05/0.01

(4) Amphiphilic compound (Tween 20)/saccharide (trehalose)=3/1 to 20/2

(5) Amphiphilic compound (Tween 20)/saccharide (pullulan) 3/0.2 to 20/2

(6) Amphiphilic compound (Tween 20)/saccharide (inulin) 3/0.1 to 20/7.

The composition for evaporation suppression of the invention is applied to the surface of a sample by painting, deposition, coating, sheathing, or the like. For example, in a case of painting, the excessive liquid is sucked up using a soft cloth-like paper such as Kimwipes, a filter paper, or the like after painting. A sample for TEM observation is treated by painting, deposition, coating, sheathing, embedding, or the like of a medium.

The film thickness of the thin film formed on the surface of a sample in this manner can be set, for example, in a range of 5 nm to 1000 nm.

Meanwhile, the "biological sample" in the description above includes prokaryotes and eukaryotes.

The prokaryotes include eubacteria and an archaebacteria.

The eubacteria include phylum Acidobacteria, phylum Aquifex, phylum Actinobateria, phylum Elusimicrobia, phylum Caldiserica, phylum Chlamydia, phylum Chlorobium, phylum Chloroflexus, phylum Chrysiogenes arsenatis, phylum Thermodesulfobacteria, phylum Thermo-microbia, phylum Cyanobacteria, Gemmatimonadetes, phylum Synergistetes, phylum Spirochaeta, phylum Dictyoglomus, phylum Thermus-Deinococcus, phylum Tenericutes, phylum Deferribacteres, phylum Thermotogae, phylum Nitrospirae, phylum Bacteroidetes, phylum Firmicutes, phylum Fibrobacteres, phylum Fusobacteria, phylum Planctomycetes, phylum Proteobacteria, phylum Verrucomicrobia, and phylum Lentisphaerae.

The archaebacteria include phylum (kingdom) Crenarchaeota, phylum (kingdom) Euryarchaeota, phylum (kingdom) Korarchaeota, phylum Nanoarchaeota, and phylum Thaumarchaeota.

The eukaryotes include kingdom Protista, kingdom Plantae, kingdom Fungi, and kingdom Animalia.

The kingdom Protista includes phylum Myxomycota, Dictyostelium discoideum, Labyrinthulomycetes, and phylum Dicontomycetes in addition to the algae (green algae, brown algae, red algae, Bacillariophyceae, division Euglena, division Cryptophyta, division Dinoflagellate), Protozoa (phylum Ciliophora, Rhizopoda (amoeba, foraminifera, heliozoan, and radiolarian), phylum Sporozoa (Apicomplexa, microsporidian, and mucus sporozoan), and flagellate (Trypanosomes, choanoflagellate, hypermastigia, and polymastigote).

The kingdom Plantae includes division Chlorophyta, division Bryophyta, division Charophyta, and subkingdom Tracheophyta (division Psilotum nudum, Lycopodiophyta, division Equisetophyta, division Ophioglossales, division Pteridophyta, division Coniferophyta (division Pinophyta), division Cycadophyta, division Ginkgophyta, division Gnetophyta, division Magnoliophyta (division Magnoliophyta (class Dicotyledoneae (class Magnoliopsida), and class Monocotyledoneae (class Liliopsida)).

The kingdom Fungi includes phylum Chytridiomycota (chytrid), phylum Zygomycota (mucor and rhizopus), phylum Ascomycota (yeast and Neurospora crassa), phylum Basidiomycota (mushroom), Fungi imperfecti, and division Lichenes.

The kingdom Animalia includes phylum Porifera, phylum Placozoa (Trichoplax adhaerens), phylum Cnidaria (jellyfish, sea anemone, and coral), phylum Ctenophora (comb jelly), phylum Mesozoa (Dicyemida), phylum Platyhelminthes (turbellaria and planarian), phylum Nemertinea (ribbon worm), phylum Gnathostomulida, phylum Gastrotricha, phylum Trochelminthes (rotifer), phylum Kinorhyncha, phylum Acanthocephala, phylum Entoprocta, phylum Nematoda (ascaris and *C. elegans*), phylum Nematomorpha (gordioidea), phylum Ectoprocta, phylum Phoronida, phylum Brachiopoda, phylum Mollusca (shellfish, squid, and octopus), phylum Priapuloidea, phylum Sipunculida (sipunculid), phylum Echiura, phylum Annelida (earthworm and lugworm), phylum Tardigrada (tardigrade), phylum Pentastoma, phylum Onychophora (velvet worm), phylum Arthropoda (sbphylum Chelicerata (superclass Pycnogonida, superclass Xiphosura (horseshoe crab), and superclass Caulogastra (spider and scorpion)), subphylum Crustacea (shrimp and crab), phylum Myriapoda (class Chilopoda (chilopoda and centipede), class Symphyla (Symphyla and symphylan), class Pauropoda (class Pauropoda and pauropoda), and class Diplopoda (class Diplopoda and millipede)), and subphylum Hexapoda (Entognata and Insecta)), phylum Pogonophora, phylum Echinodermata (sea urchin, starfish, brittle star, sea cucumber, and crinoid), phylum Chaetognatha (arrow worm), phylum Hemichordata (acorn worm), and phylum Chordata (subphylum Urochordata (sea squirt) and subphylum Cephalochordata (amphioxus), subphylum Vertebrata (superclass Agnatha (class Eptatretus and class Cephalaspidomorpha (*Petromyzon marinus*)), superclass Gnathostomata (class Chondrichthyes (shark, ray, and elephant fish), class Sarcopterygii (coelacanth and lungfish), class Actinopterygii, class Amphibia, class Reptilia, class Mammalia, and class Ayes)).

According to the sample observation method by an electron microscope of the invention, a sample can be observed using the composition for evaporation suppression described above by applying the composition for evaporation suppression on the surface of the sample to form a thin film, covering the sample with this thin film, and displaying the electron microscopic image of the sample, which is covered with this thin film and accommodated in the sample chamber under vacuum, on a display device.

Particularly, a sample can be observed by applying this composition for evaporation suppression to the surface of a sample, irradiating the sample applied with the composition for evaporation suppression with an electron beam or plasma to form a polymerized film (film of polymer) on the surface of the sample as a thin film, covering the sample with this polymerized film, and displaying the electron microscopic image of the sample, which is covered with this polymerized film and accommodated in the sample chamber under vacuum, on a display device.

This polymerized film can be formed on the surface of a sample by a polymerization reaction by irradiating the sample with the electron beam for sample observation in the sample chamber of an electron microscope.

Alternatively, this polymerized film can be formed on the surface of a sample by a polymerization reaction by irradiating the sample with an electron beam or plasma other than the electron beam for sample observation of an electron microscope in advance before observing the sample by the electron microscope.

The irradiation condition is appropriately selected depending on the composition for evaporation suppression used and the like, and is not particularly limited. As an example, a biological sample, which is not subjected to a pretreatment of the related art but is covered with the composition for evaporation suppression, is irradiated with the electron beam (for example, about 5.0 kV) of a SEM in the sample chamber for 60 minutes, and thus SEM observation (for example, observation using a general FE-SEM) of the biological sample as it is alive is possible under high vacuum (for example, $10^{-4}$ Pa to $10^{-7}$ Pa).

In addition, in another example, SEM observation or TEM observation of a biological sample as it is alive is possible under high vacuum by irradiating the biological sample, which is not subjected to a pretreatment of the related art but covered with the composition for evaporation suppression, with plasma for 3 minutes in advance.

The surface of a sample is covered with a thin polymerized film by such an irradiation of an electron beam or plasma. The thickness of this polymerized film can be set, for example, in a range of 5 nm to 1000 nm in a case in which the polymerized film is formed on the surface of a biological sample.

Polymerization by the irradiation of plasma can be performed, for example, under a condition of a pressure of $10^{-3}$ Pa to $10^{-5}$ Pa, $-20°$ C. to $+80°$ C., and 1 kV to 10 kV DC using an ion sputtering device of the related art. Alternatively, polymerization by the irradiation of plasma can be performed using a device such as a reaction tube used in the plasma polymerization of the related art or a method.

For observation by an electron microscope in the invention, a sample for SEM observation is treated by painting, deposition, coating, sheathing, or the like of the composition for evaporation suppression. For example, in a case of painting, the excessive liquid is sucked up using a soft cloth-like paper such as Kimwipes, a filter paper, or the like after painting. A sample for TEM observation is treated by painting, deposition, coating, sheathing, embedding, or the like of the composition for evaporation suppression.

According to the invention, it is possible to observe a sample without deforming and without damaging the state of the sample itself. In addition, it is possible to observe a living biological sample as it is alive using an electron microscope, and a situation that a biological sample is moving can be observed. According to the invention, the composition imparting the SS effect can suppress the loss of not only a sample for an electron microscope but also a sample under vacuum.

The composition for evaporation suppression of the invention functions as a favorable visualizing agent for sample observation by an electron microscope. In other words, the composition for evaporation suppression of the invention enables a living biological/living body sample to be accommodated in the microscope body of an electron microscope in the living state as it is without performing dehydration, chemical fixation, and electron staining of the related art, and even at the time of observation, suppresses the damage caused by drying, cryohydrate, and temperature change under decompression, and imparts the Surface Shielding Effect (SS effect) barring the water/gas in a sample.

In addition, the composition for evaporation suppression of the invention prevents charge up caused by irradiation of electron beam, and the like, and thus a favorable secondary electronic image can be acquired by electron beam irradiation under vacuum. Hence, it is possible to observe a living sample in the living state as it is at a high magnification using an electron microscope.

In other words, the composition for evaporation suppression of the invention functions as a favorable visualizing agent for sample observation by an electron microscope, and thus the composition for evaporation suppression of the invention functions is suitable for use in sample observation by a scanning electron microscope and a transmission electron microscope.

A means and a composition (reagent material) for observing the shape of a sample as it is without deforming in a sample observation method by an electron microscope, particularly for observing a biological/living body sample in the living state as it is, are provided.

A protective film is formed on the surface of a biological sample by a chemical substance. The film prevents the water or air (gaseous substance) contained in the biological sample from leaking under vacuum. The film can be formed under an atmospheric pressure condition or a vacuum condition, and the film thus formed is tougher under vacuum. The film can be formed as a single film or a multilayered film.

A method such as covering with an inorganic substance (ceramics) may be used in order to separate the outer system from the inner system. In this method, there is a case in which the movement of a sample is inhibited since the surface is hard, or the sample perishes because of difficulty in breathing in a case of a living sample. On the contrary, in the invention, a method, in which the sample is uniformly covered with a bag-like film, and thus the problem described above is solved.

The composition for evaporation suppression of the invention imparts barrier performance with respect to the evaporable substance such as water or gas in the body of a living being under atmospheric pressure and vacuum. By the performance, the evaporation of the substance in the living being can be prevented under vacuum. Hence, decrease in temperature associated with evaporation can be prevented and thus motility is provided. Moreover, the shape of the biological sample is preserved as it is, and the internal body temperature, which enables the biological sample to be active, can be maintained even under decompression.

In a case in which a sample is covered with the composition for evaporation suppression of the invention, it is possible to coat a biological sample as it is alive if the sample is a living being, and the living being is alive even after coating. A biological sample can be observed in the living state using a scanning electron microscope, and the structure such as the micro surface of the biological sample can also be observed by covering the body surface of the living biological sample with a thin film formed of the composition for evaporation suppression of the invention.

Moreover, it is possible to directly observe a biological sample in the living state using a scanning electron microscope without charge up by covering the body surface of the living biological sample with the composition for evaporation suppression of the invention.

In addition, the composition for evaporation suppression of the invention enables the observation of a biological/living body sample at a high magnification without performing the processes such as chemical fixation→conductive staining→dehydration→drying→coating or chemical fixation→dehydration→embedding→ultrathin sectioning→electron staining→coating, which have been required for observation by an electron microscope so far and required for sample preparation.

The composition for evaporation suppression of the invention enables the electron microscopic observation of not only a biological sample but also a hydrated sample in a wet state as it is under vacuum without accompanying collapse of the sample.

The composition for evaporation suppression of the invention suppresses the deformation and transformation of a sample even during observation by an electron microscope, and thus the sample is not seriously damaged before and after observation. The composition for evaporation suppression of the invention suppresses significant decrease in water/gas barrier performance and internal body temperature of the sample under vacuum, exerts suppression of decrease in water/gas barrier performance and internal body temperature of the sample under vacuum although an electron beam is irradiated, and prevents charge up and suppresses thermal damage caused by irradiation of electron beam. In a case in which the sample is a biological sample, the biological sample in the living state can be observed as it is alive, and thus any change on the sample is not recognizable even when the sample is taken out from the microscope body.

In the invention, the sample observation by a scanning electron microscope and a transmission electron microscope can be performed using an apparatus having a known configuration.

A scanning electron microscope generally includes a body tube part (microscope body) and an operation part. In the body tube part, an electron beam is generated by an electron gun, the electron beam is focused by an electron lens, an electron probe is trimmed, and the scanning of electron probe at the observation region on the surface of a sample is performed by a deflection coil. A sample chamber, in which a sample is mounted, is equipped with a sample stub and a detector detecting the signal released from a sample. This body tube part is provided with a vacuum pumping mechanism corresponding to the intended use since the body tube pat should be maintained in a clean vacuum.

The operation part controls the generation of an electron beam, the lens function of an electron lens, astigmatism correction, the scanning range (magnification) or scanning speed of the electron probe on the surface of a sample, and displays the signal detected on CRT as a video image.

In addition, in a case of a still image of a scanning electron microscope, observation and photographing is generally performed in a slow scanned image having little noise, but observation in a TV mode, that is, a moving video image is primary in the observation of a living biological sample by a scanning electron microscope. Hence, it is also considered that the scanning electron microscope is additionally provided with a TV mode image display and recording circuit having little noise (small S/N), and display and recording of an image of the scanning electron microscope is performed in a high quality TV mode.

In the invention, the sample observation by a scanning electron microscope and a transmission electron microscope can also be performed using an apparatus having a known configuration so far, and the apparatus having a new configuration, which is described below, is suitable for the method of the invention.

Figure 22:
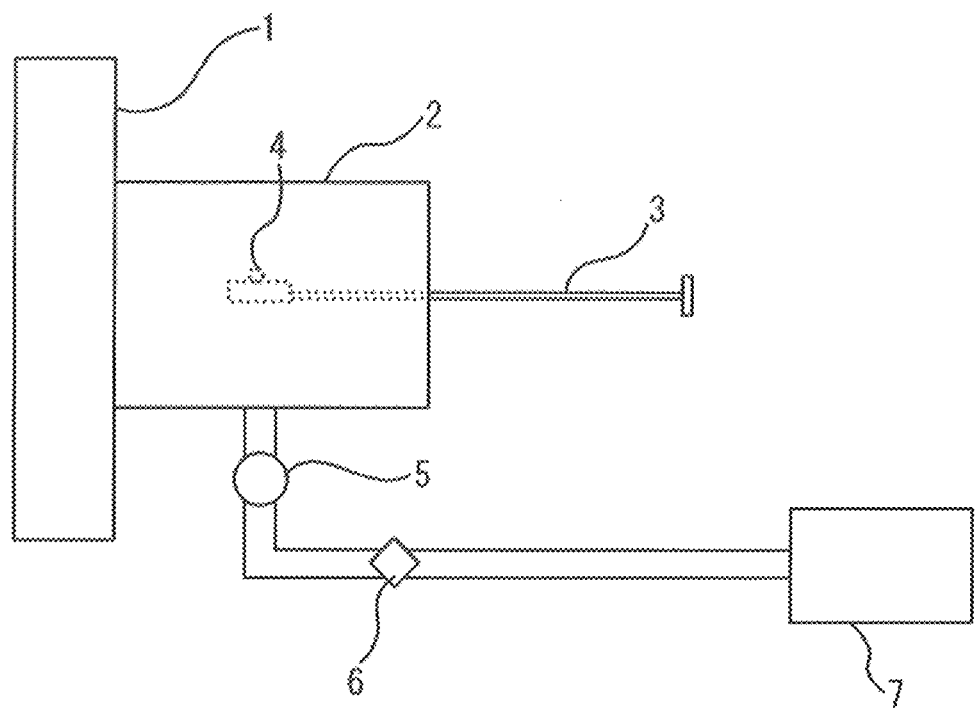
FIG. 22 is a diagram schematically illustrating a main part of one embodiment of a scanning electron microscope of the invention.

FIG. 22 is a diagram schematically illustrating a main part of one embodiment of a scanning electron microscope of the invention. This scanning electron microscope (SEM) 1 includes a preliminary exhaust chamber 2 capable of being introduced with a sample 4 to be mounted in a sample chamber in the microscope body, and an exhauster 7 deaerating the sample chamber and the preliminary exhaust chamber 2.

In the sample observation by SEM 1, a sample is set inside of the sample chamber to be observed, and a preliminary exhaust chamber 2 is provided between the sample chamber and the outside as a sample exchange chamber in order to maintain the sample chamber in high vacuum, and the sample 4 is taken in and out by a sample exchange bar 3.

This preliminary exhaust chamber 2 is connected with the exhauster 7 such as a vacuum pump, a control valve 6 such as a needle valve is equipped in the exhaust pathway between the preliminary exhaust chamber 2 and the exhauster 7, and a vacuum gauge 5 such as a pirani vacuum gauge is equipped on the exhaust upstream side of the control valve 6. As described above, it is configured such that a mechanism, in which the sample chamber and the preliminary exhaust chamber 2 are gradually deaerated by the exhauster 7, is provided, and thus the degree of vacuum is constantly maintained, and different works can be performed at different degrees of vacuum.

In a case in which a biological sample is observed using the SEM 1, the biological sample should be delivered from the atmospheric pressure condition to the vacuum condition. However, not only a living body sample but even an ultra-structural body is put to trouble by pressure change or wind pressure at the time of exhaust. Consequently, it is required that a mechanism, in which vacuum exhaust is more gently performed, is provided.

In view of such a circumstance, in this embodiment, a mechanism, in which the vacuum gauge 5 and the control valve 6 are combined, is provided in SEM 1, so that the speed of vacuum exhaust can be controlled until achieving the vacuum degree of the rotary pump region. This device (usable at different degrees of vacuum), in which exhaust is stepwisely performed, is preferably configured such that the sample chamber and the preliminary exhaust chamber 2 are large in size, a high functional vacuum pump is equipped so that the large chambers are effectively vacuumed, and the degree of vacuum can be instantly controlled.

Figure 23:
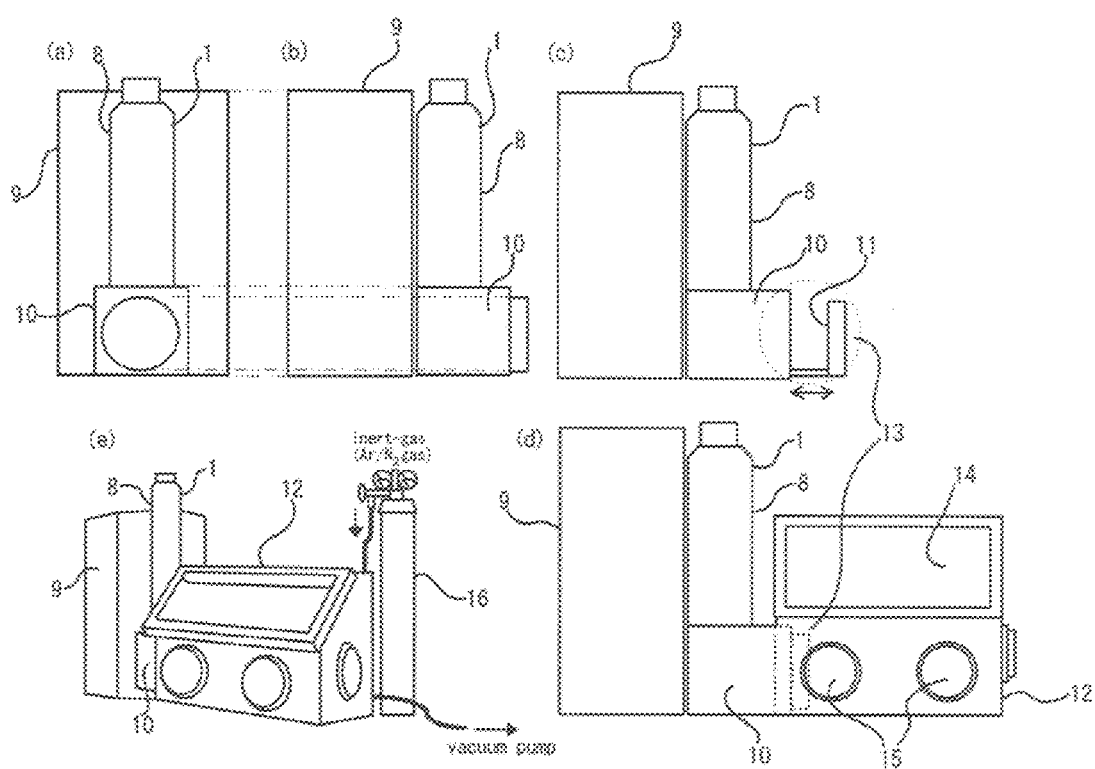
FIGS. 23(a) to 23(e) are diagrams schematically illustrating a main part of another embodiment of a scanning electron microscope of the invention.

FIGS. 23(a) to 23(e) are diagrams schematically illustrating a main part of another embodiment of a scanning electron microscope of the invention. FIG. 23(a) is a front view of the SEM main body and power source, FIG. 23(b) is a side view thereof, FIG. 23(c) is a side view of the state in which a glove box is detached, FIG. 23(d) is a side view of the state in which a glove box is attached, and FIG. 23(e) is a perspective view illustrating the state in which an inert gas cylinder is attached to a glove box.

In this embodiment, the preliminary exhaust chamber 2 is equipped with a glove box 12. It is possible to perform work in a vacuum by equipping the preliminary exhaust chamber 2 with a glove box 12.

As illustrated in FIGS. 23(c) and 23(d), the sample chamber 10 at the lower part of a microscope body 8 of SEM 1 attached with the power source 9 is provided with the glove box 12 alongside such that a sample folder 11 is accommodated in a housing 14 in the glove box 12.

The glove box 12 has a work port 15, which is attached with a rubber glove or the like, and window part 14, through which the inside can be seen, so that work dealt with a sample is possible under vacuum. Moreover, a sample can be introduced into the sample chamber in the SEM 1 from the inside of the glove box 12 as a sample introducing part by the sample folder 11 without exposing the thin film covering the sample to atmospheric pressure. For example, plasma polymerized film can be formed in the glove box 12 connected to SEM 1.

In addition, the glove box 12 enables a sample to be handled under vacuum, and, as described in FIG. 23(e), it is also possible that the glove box 12 is equipped with the inert gas cylinder 16, which is capable of being introduced with an inert gas such as argon or nitrogen, and thus the inside of the glove box 12 is purged with an inert gas, and then used. This is suitable for plasma treatment and the like. For example, when a polymerized film is formed on the surface of a sample by a polymerization reaction in the preliminary exhaust chamber 2, the reaction can be controlled by filling the glove box with a specific gas such as nitrogen and argon.

Figure 24:
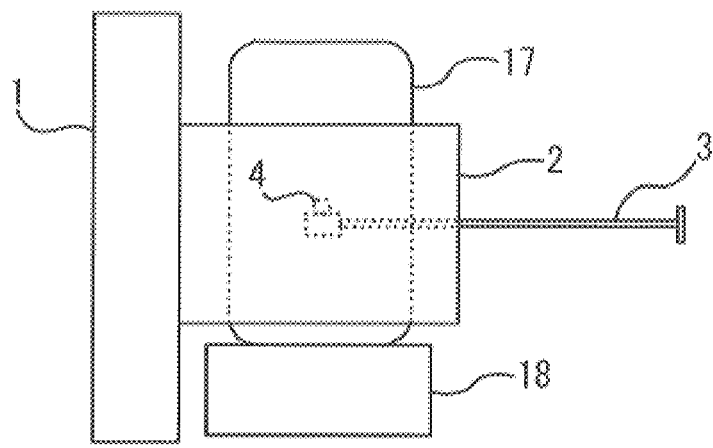
FIG. 24 is a diagram schematically illustrating a main part of still another embodiment of a scanning electron microscope of the invention.

FIG. 24 is a diagram schematically illustrating a main part of still another embodiment of a scanning electron microscope of the invention. In this embodiment, the preliminary exhaust chamber 2 is equipped with plasma irradiation device or electron irradiation device 18.

Meanwhile, the sample chamber of SEM 1 may be equipped with this plasma irradiation device or electron irradiation device 18.

In addition, the preliminary exhaust chamber 2 is equipped with a transparent bell jar 17. Plasma or an electron beam can be irradiated from the plasma irradiation device or electron irradiation device 18 via this transparent bell jar 17.

For example, the plasma irradiation device can be configured such that a handy type plasma irradiation device, of which the irradiation portion is held in hand, is additionally equipped in addition to a plasma irradiation device of the related art, which is used in ion etching and of which the irradiation portion is fixed, and thus each of them can be used. Moreover, the plasma irradiation device can be configured such that the irradiation diameter of plasma can be adjusted in a range of several nm to several tens cm, and thus the area and intensity of irradiation can be changed according to the size of the sample 4, as a result, a device, in which not only the amperage can be controlled but also the size of the irradiation diameter itself can be changed, is provided.

The sample stub to be mounted with the sample 4 may be have a function rotating three dimensionally so that the entire surface of the sample can be uniformly polymerized by the irradiation of an electron beam or plasma. Alternatively, design, in which an electron beam or plasma can pass through the sample stub, can be applied so that the polymerization is performed to the rare face of the sample. In addition, a CCD camera recording work in the preliminary exhaust chamber 2 is equipped, and thus the situation of the sample 4 in a preliminary exhaust state and the situation of the plasma irradiation can be monitored.

As the examples described above, the irradiation time or the amperage of the plasma irradiation device or electron irradiation device 18 can be automatically or manually controlled by incorporating a device, by which plasma or an electron beam can be irradiated in various conditions, to the preliminary chamber 2.

Figure 25:
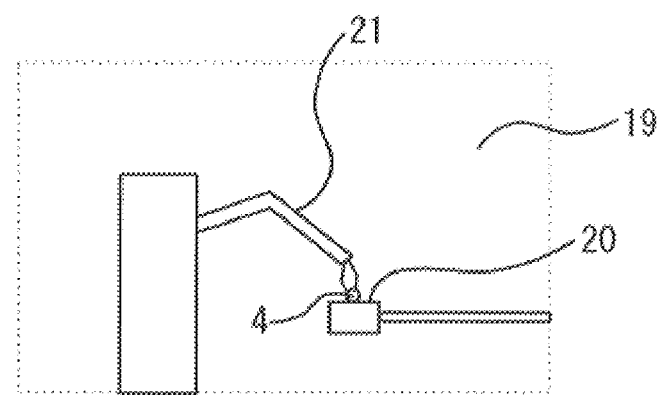
FIG. 25 is a diagram schematically illustrating a main part of yet another embodiment of a scanning electron microscope of the invention.

FIG. 25 is a diagram schematically illustrating a main part of yet another embodiment of a scanning electron microscope of the invention. In this embodiment, a sample chamber inside 19 is equipped with a three dimensional manipulator 21 capable of operating on the sample 4.

Meanwhile, the preliminary exhaust chamber 2 may be equipped with this three dimensional manipulator 21.

This three dimensional manipulator 21 is used for the control (including reduction of picture blur at the time of observation and photographing) of the movement of a sample, such as a living biological sample, as an object.

This three dimensional manipulator 21 can also be used in microvivisection, stimulation, and biological signal derivation.

Figure 26:
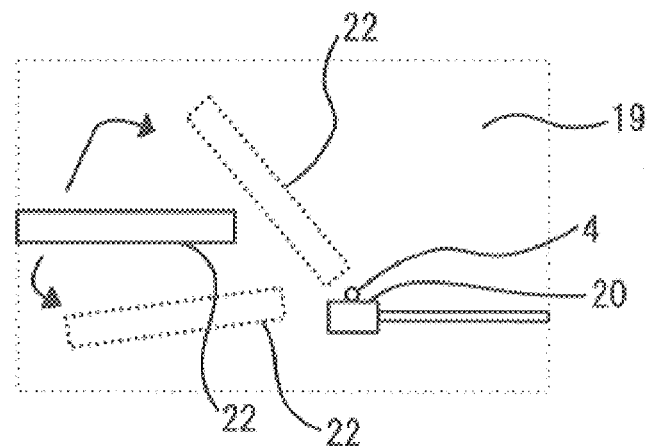
FIG. 26 is a diagram schematically illustrating a main part of still yet another embodiment of a scanning electron microscope of the invention.

For example, the sample chamber inside 19 can be equipped with the three dimensional manipulator 21 as a transfer mechanism for transferring a member used in the transfer of a sample, the microdissection of a sample, or physical or chemical stimulation. A device, in which reaction experiment can be initiated while an electron beam is generated and a secondary electron image or the like is observed, is required in order to dynamically observe the reaction such as contact and permeation a reagent to a biological sample using the SEM 1. Hence, the three dimensional manipulator 21 as a transfer mechanism can be used as a device performing the fine dissection of the sample 4, physical or chemical stimulation, and the like while observing using the SEM 1. FIG. 26 is a diagram schematically illustrating a main part of still yet another embodiment of a scanning electron microscope of the invention. In this embodiment, the sample chamber inside 19 is equipped with a detection position regulatory mechanism capable of three dimensionally regulating the relative position of a secondary electron detector 22 and the sample 4.

The detection position regulatory mechanism enables the secondary electron detector 22 to transfer in the SEM 1, and if necessary, brings the secondary electron detector 22 close to the sample 4 or into contact with the sample 4 at a special angle. Consequently, the detected secondary electron can be intensified.

This detection position regulatory mechanism is suitable to be equipped with a high speed photography device. In other words, since this detection position regulatory mechanism is a TV mode in which the scanning speed can increase and slow reproduction is possible, the area control of the detector and the control of working distance to the detector, and the like are possible, and the secondary electrons can be collected without waste. Software characterizing the movement by taking the finite difference of before and behind, and the like can also be applied as an interpolation technique.

Figure 27:
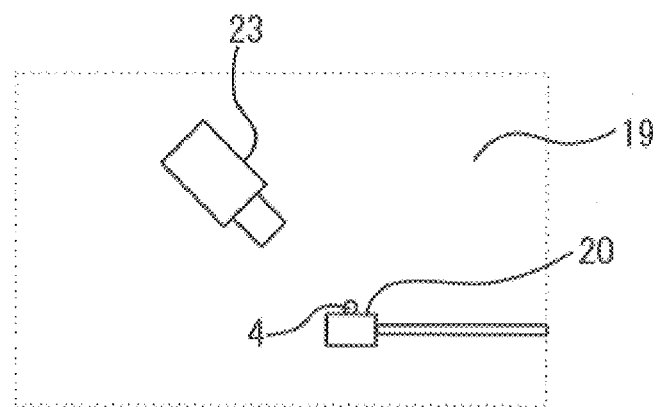
FIG. 27 is a diagram schematically illustrating a main part of further embodiment of a scanning electron microscope of the invention.

FIG. 27 is a diagram schematically illustrating a main part of further embodiment of a scanning electron microscope of the invention. In this embodiment, the sample chamber inside 19 is equipped with a high speed color camera 23 capable of acquiring color information of the sample 4.

According to the invention, the color of the sample 4 is preserved as it is since the sample 4 can be observed as it is alive. Hence, the sample chamber inside 19 is equipped with a high speed color camera 23 so that the information such as colors can also be recorded, and thus the actual colors recorded can be applied to the image observed by SEM as pseudo colors.

Figure 28:
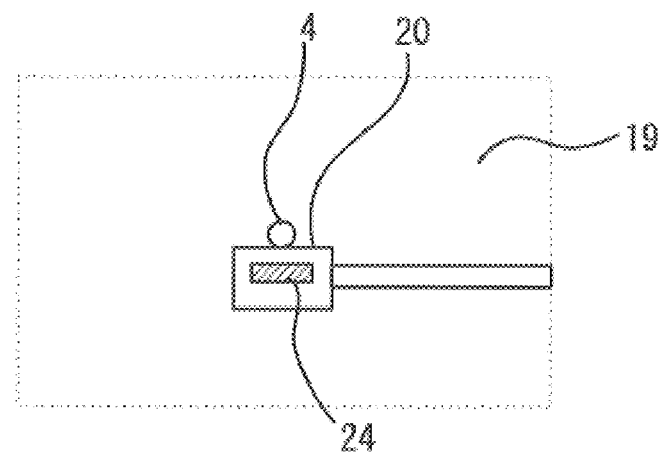
FIG. 28 is a diagram schematically illustrating a main part of further another embodiment of a scanning electron microscope of the invention.

FIG. 28 is a diagram schematically illustrating a main part of further another embodiment of a scanning electron microscope of the invention. In this embodiment, the scanning electron microscope includes a temperature regulator 24 capable of regulating the temperature of the sample stub 20 of the sample chamber inside 19.

For example, a stage, which can control the temperature of the sample stub 20 between −20° C. to 100° C. at the outside of the microscope body, and which is not affected by a magnetic field, can be equipped. Specifically, for example, a Peltier element and the like can be equipped as a device maintaining the temperature of the sample stub 20 at a constant value (for example, 37° C.).

The temperature of the sample 4, such as a biological sample, mounted on the sample stub 20 can be regulated by this temperature regulator 24.

Figure 29:
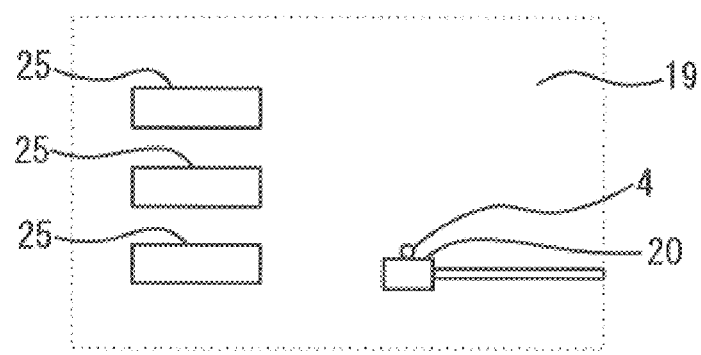
FIG. 29 is a diagram schematically illustrating a main part of further still another embodiment of a scanning electron microscope of the invention.

FIG. 29 is a diagram schematically illustrating a main part of further still another embodiment of a scanning electron microscope of the invention. In this embodiment, the sample chamber inside 19 is equipped with various sensors 25.

Examples of the sensor 25 may include an electrical sensor, a light sensor, a gas sensor, a water sensor, and a temperature sensor. In addition, a highly sensitive sensor (with dark field camera) capable of measuring at week light can be equipped.

By this sensor 25, the information of the sample 4, such as a biological sample, mounted on the sample stub 20 can be acquired, and the monitoring or measurement of the response to the physical or chemical stimulation and the like, polymerization reaction, and the like can be performed.

Figure 30:
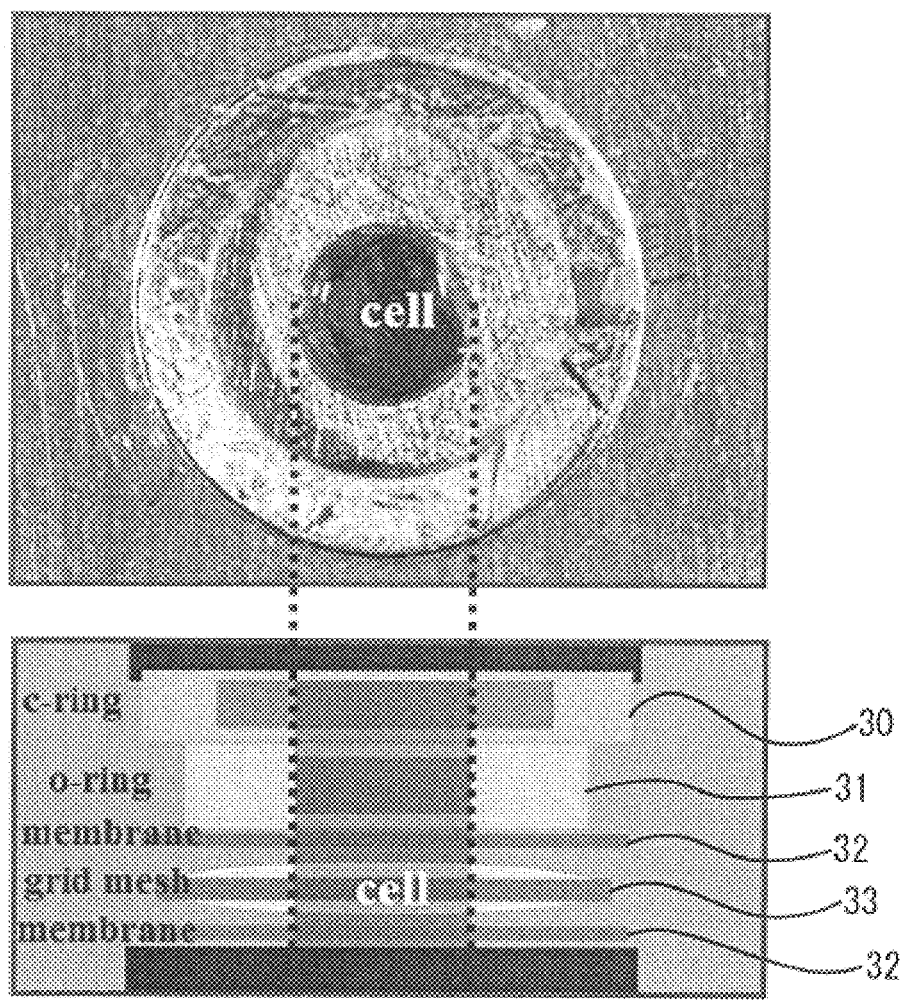
FIG. 30 is a diagram schematically illustrating a main part of one embodiment of a transmission electron microscope of the invention.
Figure 31:
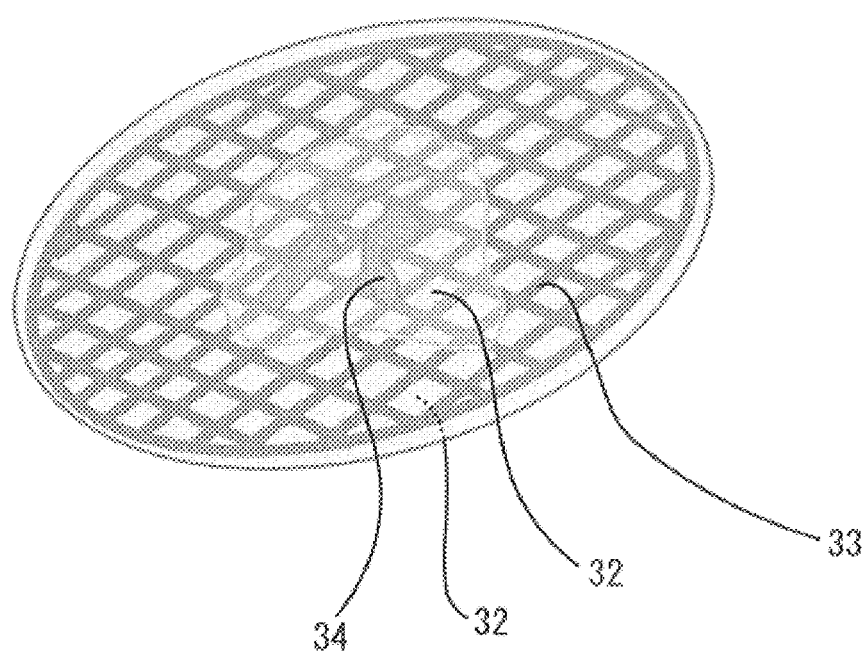
FIG. 31 is a perspective view schematically illustrating the main part of FIG. 30.

FIG. 30 is a diagram schematically illustrating a main part of one embodiment of a transmission electron microscope of the invention, and FIG. 31 is a perspective view schematically illustrating the main part of FIG. 30. In this embodiment, each of the both sides of a grid mesh 33 to be mounted with a sample has a polymerized film 32 formed by irradiating the composition for evaporation suppression with an electron beam or plasma.

As illustrated in FIG. 30, a sandwich-like sample folder for TEM has a C-ring 30 and O-ring 31, of which the lower place is mounted with the grid mesh 33 interposed with an upper polymerized film and a lower polymerized film 32. The polymerized film 32 can be sealed by, for example, vacuum grease and the O-ring.

As illustrated in FIG. 31, the polymerized film 32 is layered on the grid mesh 33 by plasma, cells 34, a sample, is superimposed on the polymerized film 32, further the composition for evaporation suppression is applied thereon, and plasma is irradiated to form the polymerized film 32 on the cells 34. For example, a transmission electron microscope can includes a preliminary exhaust chamber capable of being introduced with a sample to be mounted in a sample chamber in the microscope body, and an exhauster deaerating the sample chamber and the preliminary exhaust chamber in the same manner as the SEM of FIG. 22. In addition, the sample chamber or the preliminary exhaust chamber is equipped with a plasma irradiation device or an electron beam irradiation device in the same manner as the SEM of FIG. 24. As described above, the polymerized film 32 can be formed by applying the composition for evaporation suppression and irradiating plasma after modifying the TEM such that a plasma or electron beam polymerization can be performed in the preliminary exhaust chamber of the TEM. The irradiation diameter of plasma can be adjusted in a range of several nm to several tens cm, and thus the area of irradiation can be changed according to the size of a sample. In addition, dynamic analysis as it is alive can be performed even in a high vacuum by sealing a target cell and a culture solution in the sample folder by such a method. A sample bonded with colloidal gold can also be observed. In addition, a long time observation is possible by modifying a Scanning Transmission Electron Microscope (STEM) and reducing the dose of electron beam irradiated to a living sample introduced in the TEM.

EXAMPLES

Hereinafter, the invention will be described in further detail with reference to Examples, but the invention is not limited to these Examples.

In Examples below, SEM observation was typically performed using a field emission-type scanning electron microscope (FESEM, S-4800 (Hitachi)) at an acceleration voltage of 5.0 kV. In order to record the dynamic movement of a biological sample, the image data of SEM was directly transferred to a video recorder (Hi-band digital formatted video recorder, Pioneer, DVR-DT95).

TEM observation was typically performed using JEM-1220 (JEOL) at an acceleration voltage of 120 kV.

Plasma polymerization was typically performed by an ion sputtering device (JFC-1100, JEOL), in which the metallic target was disjointed, and plasma irradiation was performed in a vacuum level of about 1.0 Pa, at room temperature and 1.0 kV DC (8.0 mA) for 3 minutes.

Example 1

A composition for evaporation suppression was prepared using a 0.1% aqueous solution of sodium laurylbenzenesulfonate as an amphiphilic compound and 0.01 wt % of ethylenediamine nickel complex as a metal compound.

A living leaf beetle was immersed in the composition for evaporation suppression for 1 minute, taken out therefrom, and the excess was wiped off, thereby covering the body surface of the leaf beetle with a thin film.

Thereafter, the leaf beetle covered with a thin film was introduced in the sample chamber of a SEM, and videotaped (FIG. 1). The situation that the leaf beetle was moving was observed even after the initiation of electron beam irradiation.

Moreover, the leaf beetle was alive even after taken out from the sample chamber after SEM observation.

Example 2

A composition for evaporation suppression was prepared using a 0.1% aqueous solution of sodium laurylbenzenesulfonate as an amphiphilic compound and 0.01 wt % of ethylenediamine nickel complex as a metal compound.

A living collembolan was immersed in the composition for evaporation suppression for 1 minute, taken out therefrom, and the excess was wiped off, thereby covering the body surface of the collembolan with a thin film.

Figure 2:
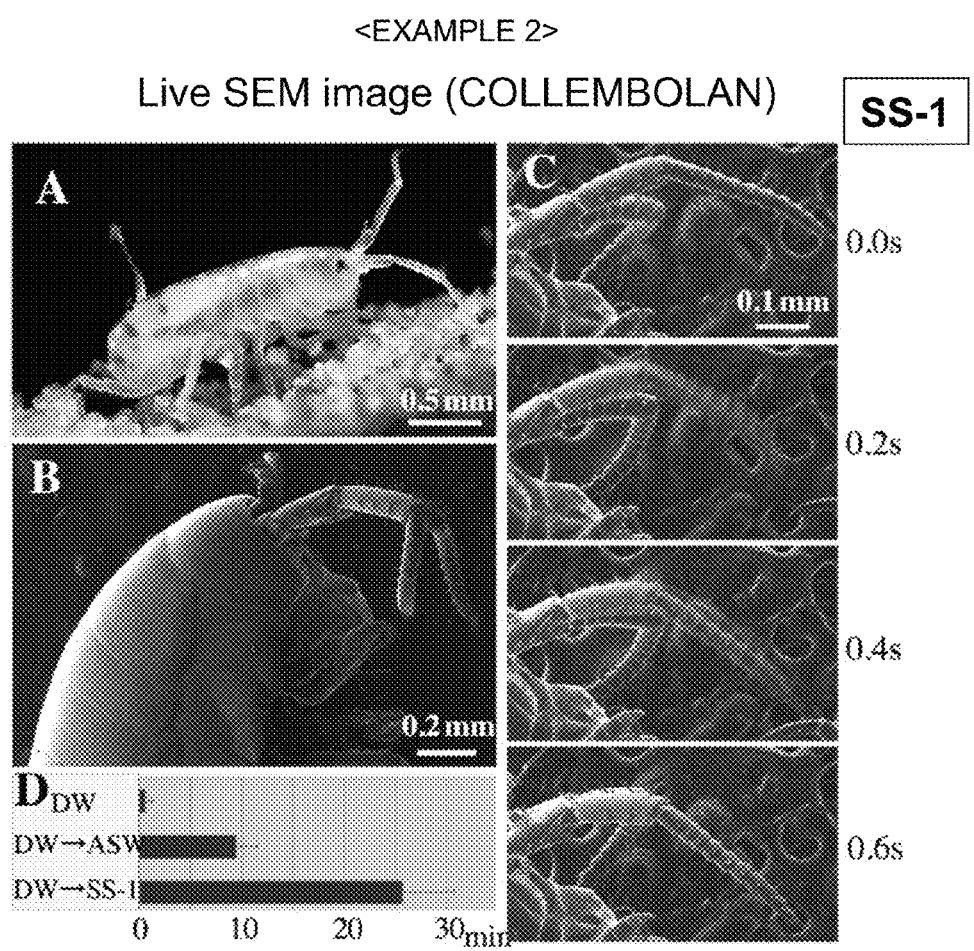
FIG. 2 is a photograph illustrating the situation of SEM video of Example 2.

Thereafter, the collembolan covered with a thin film was introduced in the sample chamber of a SEM, and videotaped (FIG. 2). The situation that the collembolan was moving was observed even after the initiation of electron beam irradiation.

Moreover, the collembolan was alive even after taken out from the sample chamber after SEM observation.

Example 3

A composition for evaporation suppression was prepared using a 10% aqueous solution of Tween 20 as an amphiphilic compound, and 1% (w/v) of trehalose and 0.1% (w/v) of pullulan as saccharides.

A living larva of Polypedilum vanderplanki was immersed in the composition for evaporation suppression for 1 minute, taken out therefrom, and the excess was wiped off, thereby covering the body surface of the larva of Polypedilum vanderplanki with a thin film.

Figure 3:
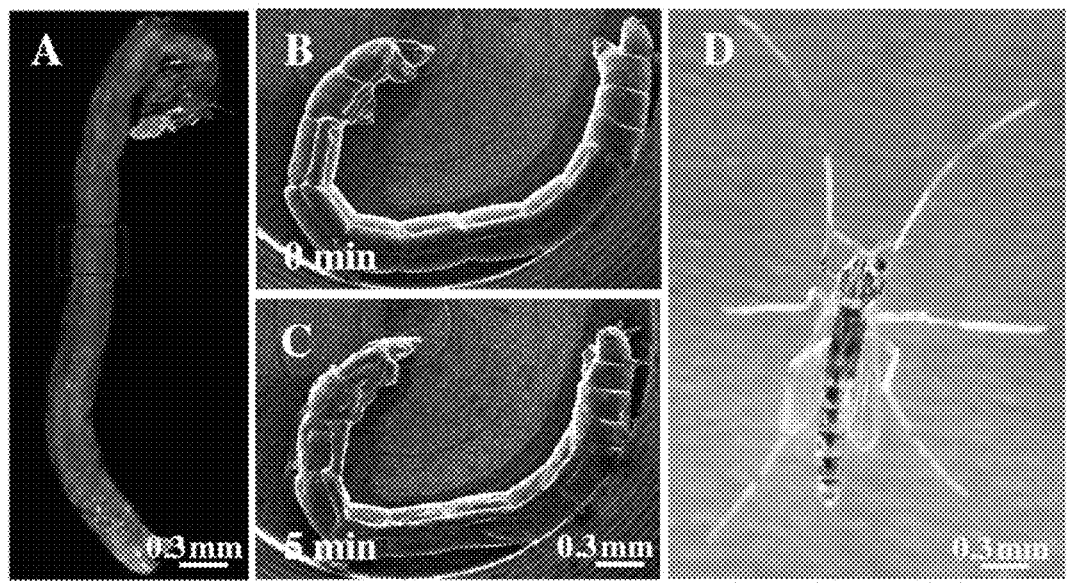
FIG. 3 is a photograph illustrating the situation of SEM video of Example 3.

Thereafter, the larva of Polypedilum vanderplanki covered with a thin film was introduced in the sample chamber of a SEM, and videotaped (FIG. 3). The situation that the larva of Polypedilum vanderplanki was moving was observed even after the initiation of electron beam irradiation.

Moreover, the larva of Polypedilum vanderplanki was alive even after taken out from the sample chamber after SEM observation, and was metamorphosed into an imago.

Example 4

A composition for evaporation suppression was prepared using a 10% aqueous solution of Tween 20 as an amphiphilic compound, and 1% (w/v) of trehalose and 0.1% (w/v) of pullulan as saccharides.

A living larva of wiggle tail (*Aedes albopictus*) was immersed in the composition for evaporation suppression for 1 minute, taken out therefrom, and the excess was wiped off, thereby covering the body surface of the larva of wiggle tail with a thin film.

Figure 4:
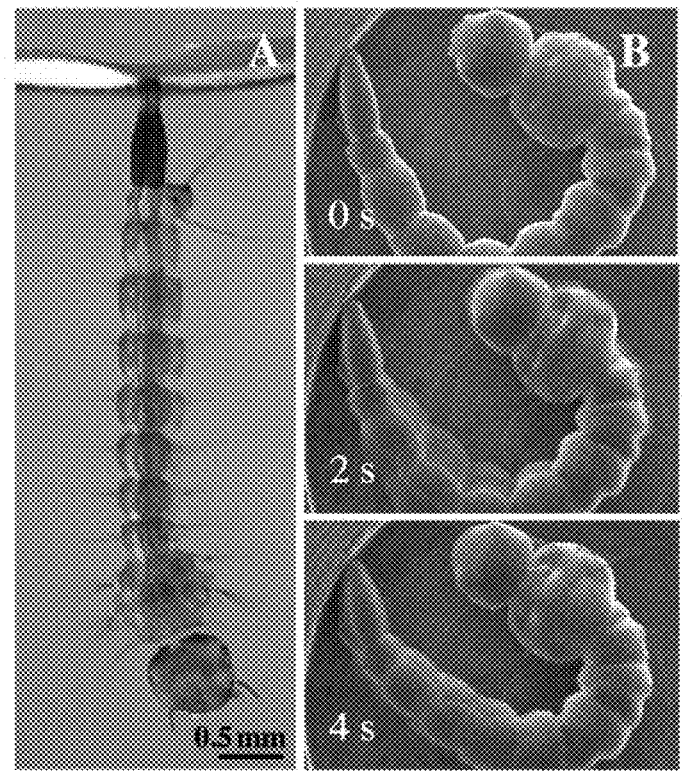
FIG. 4 is a photograph illustrating the situation of SEM video of Example 4.

Thereafter, the larva of wiggle tail covered with a thin film was introduced in the sample chamber of a SEM, and videotaped (FIG. 4). The situation that the larva of wiggle tail was moving was observed even after the initiation of electron beam irradiation.

Moreover, the larva of wiggle tail was alive even after taken out from the sample chamber after SEM observation, and was metamorphosed into an imago.

Example 5

A composition for evaporation suppression was prepared using a 10% aqueous solution of Tween 20 as an amphiphilic compound, and 1% (w/v) of trehalose and 0.1% (w/v) of pullulan as saccharides.

A living larva of wiggle tail was immersed in the composition for evaporation suppression for 1 minute, taken out therefrom, and the excess was wiped off, thereby covering the body surface of the larva of wiggle tail with a thin film.

Figure 5:
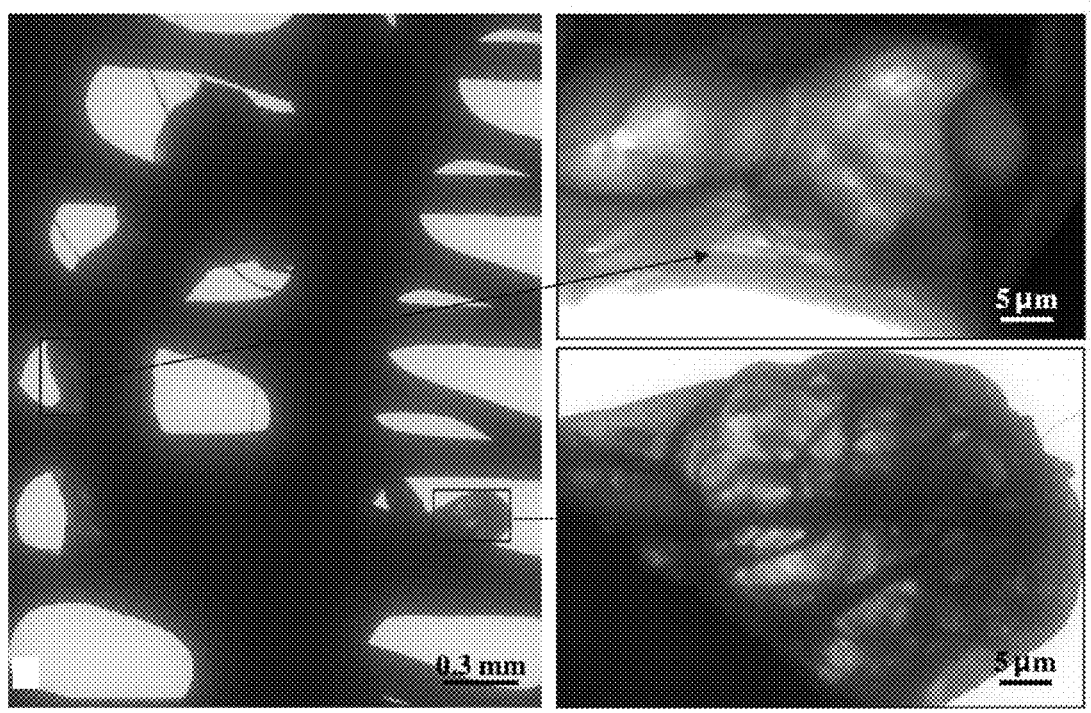
FIG. 5 is a photograph illustrating the situation of TEM video of Example 5.

Thereafter, the larva of wiggle tail covered with a thin film was introduced in the sample chamber of a TEM, and videotaped (FIG. 5). The situation that the larva of wiggle tail was moving was observed even after the initiation of electron beam irradiation.

Example 6

A composition for evaporation suppression was prepared using a 0.1% aqueous solution of sodium laurylbenzenesulfonate as an amphiphilic compound and 0.01 wt % of ethylenediamine nickel complex as a metal compound.

Figure 6:
FIG. 6 is a photograph illustrating the situation of SEM video of Example 6.
Figure 6:
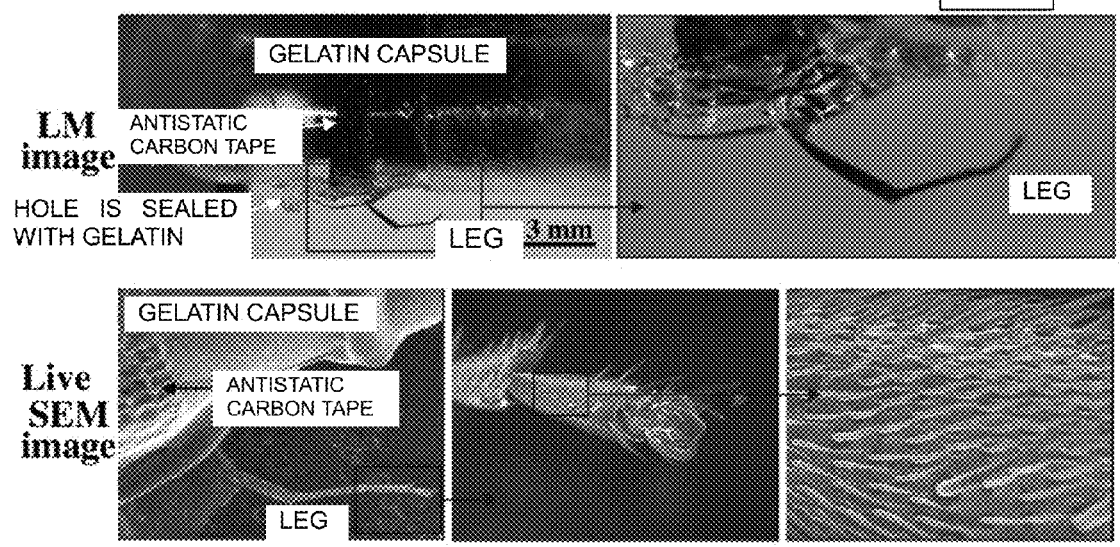

An ant was encapsulated with a gelatin capsule, fixed with an antistatic carbon tape, and the hole was sealed with gelatin. In this manner, only a leg of the observation part was put out from the capsule, and this leg part was coated with the composition for evaporation suppression, and then SEM observation thereof as it is alive was performed while preserving the air in the gelatin capsule introduced with an ant. It was possible to videotape the movement of the leg part (FIG. 6).

Moreover, the ant was alive even after taken out from the sample chamber after SEM observation.

Example 7

A composition for evaporation suppression was prepared using a 0.1% aqueous solution of sodium laurylbenzenesulfonate as an amphiphilic compound and 0.01 wt % of ethylenediamine nickel complex as a metal compound.

Figure 7:
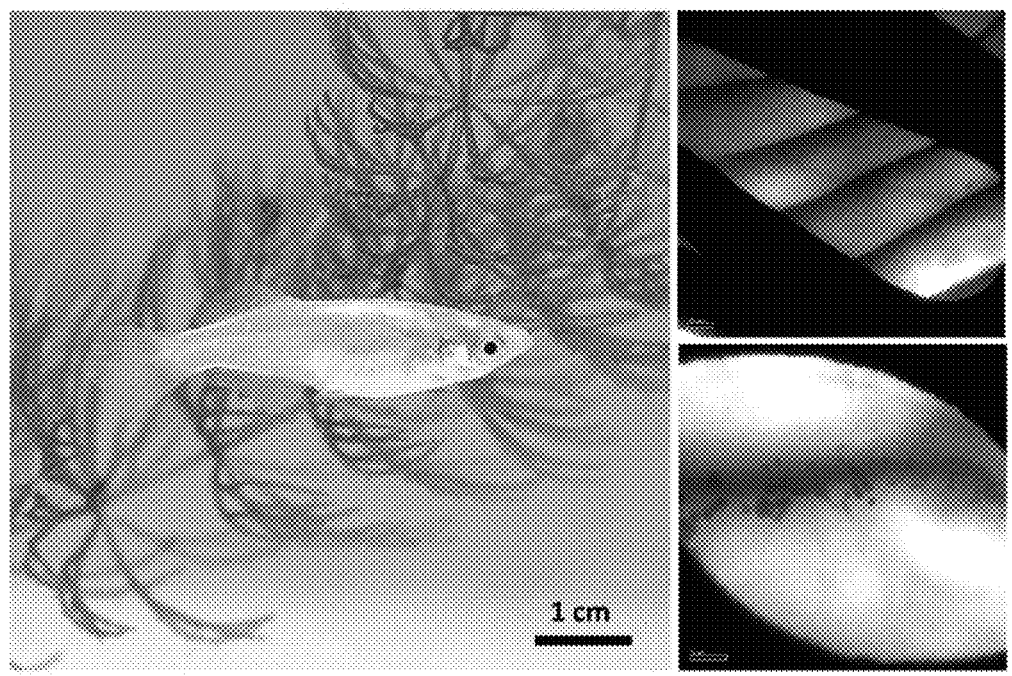
FIG. 7 is a photograph illustrating the situation of TEM video of Example 7.

A scale of living *Oryzias latipes* was immersed in the composition for evaporation suppression for 1 minute. Thereafter, the scale covered with the composition for evaporation suppression was introduced in the sample chamber of a TEM, and videotaped (FIG. 7). The situation that the internal ultrastructure of the scale was changing was observed even after the initiation of electron beam irradiation.

Example 8

A composition for evaporation suppression was prepared using a 10% aqueous solution of Tween 20 as an amphiphilic compound, and 1% (w/v) of trehalose and 0.1% (w/v) of pullulan as saccharides.

Figure 8:
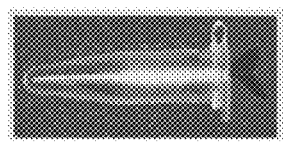
FIG. 8 is a photograph illustrating the situation of SEM video of Example 8.
Figure 8:
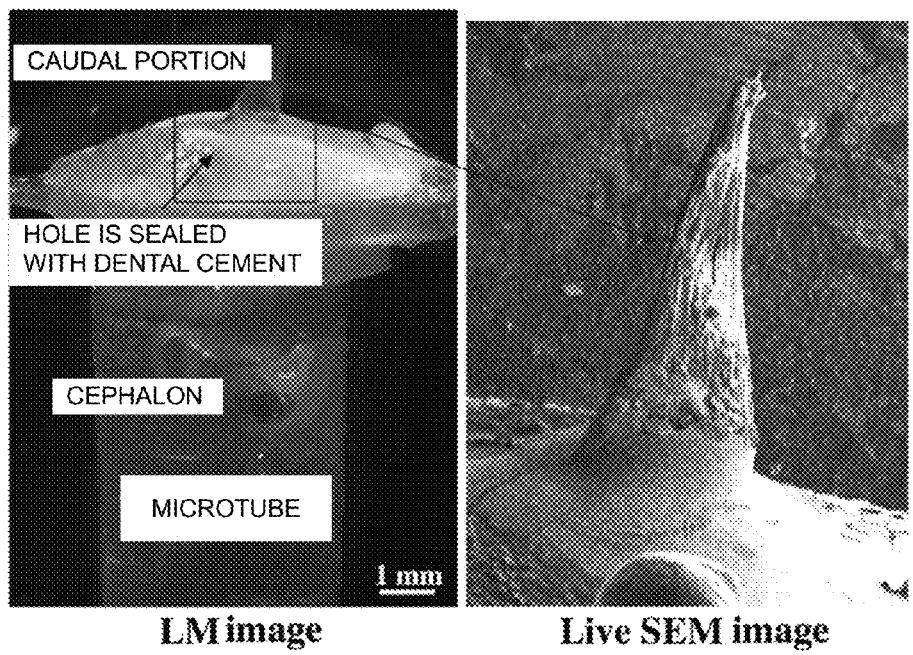

A guppy was encapsulated in a microtube together with the breeding water, and only the caudal fin was put out from the microtube and the hole was sealed with dental wax. In this manner, only the caudal fin of the observation part was put out from the microtube, this caudal fin was coated with the composition for evaporation suppression, and then SEM observation thereof as it is alive was performed while preserving the air and water system in the microtube introduced with a guppy. It was possible to videotape the movement of the caudal fin even after the initiation of electron beam irradiation (FIG. 8).

Moreover, the guppy was alive even after taken out from the sample chamber after SEM observation.

Example 9

A composition for evaporation suppression was prepared using a 10% aqueous solution of Tween 20 as an amphiphilic compound, and 1% (w/v) of trehalose and 0.1% (w/v) of pullulan as saccharides.

Figure 9:
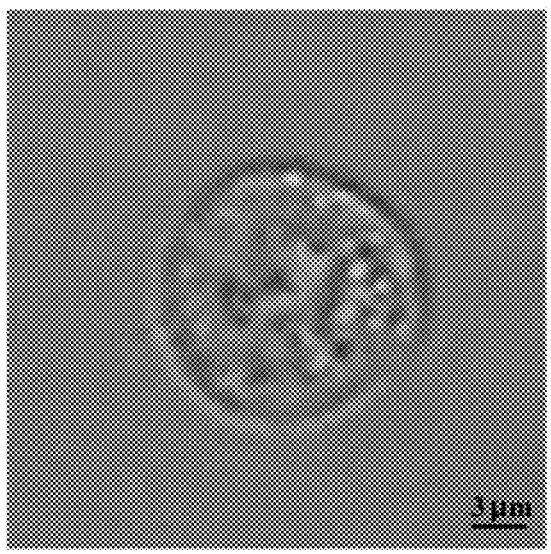
FIG. 9 is a photograph illustrating the situation of TEM video of Example 9.
Figure 9:
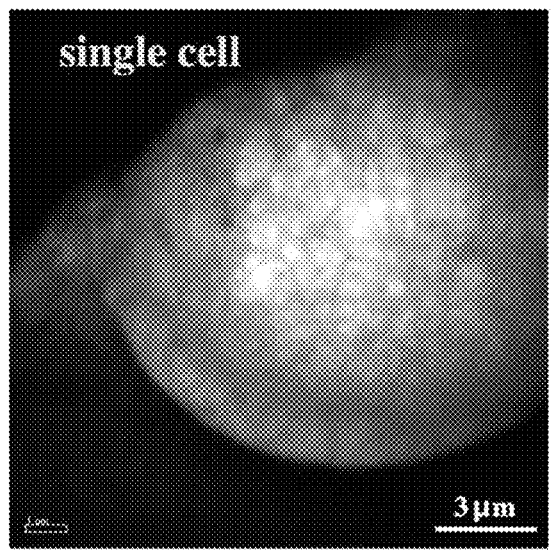

An ectodermal epithelial cell of hydra was immersed in the composition for evaporation suppression for 1 minute. Thereafter, the ectodermal epithelial cell of hydra covered with the composition for evaporation suppression was introduced in the sample chamber of a TEM, and the ectodermal epithelial cell of hydra as it is alive was videotaped even after the initiation of electron beam irradiation (FIG. 9). Among the drawings, the left is the optical microscopic image and the right is the video image of TEM. The ectodermal epithelial cell of hydra was directly irradiated with an electron beam (120 kV) for 3 minutes under high vacuum after performing the treatment described above but without performing a pretreatment of the related art.

Example 10

Fats and oils were used as a composition for evaporation suppression.

A living planarian was immersed in the composition for evaporation suppression (silicon oil) for 1 minute, taken out therefrom, and the excess was wiped off, thereby covering the body surface of the living planarian with a thin film.

Figure 10:
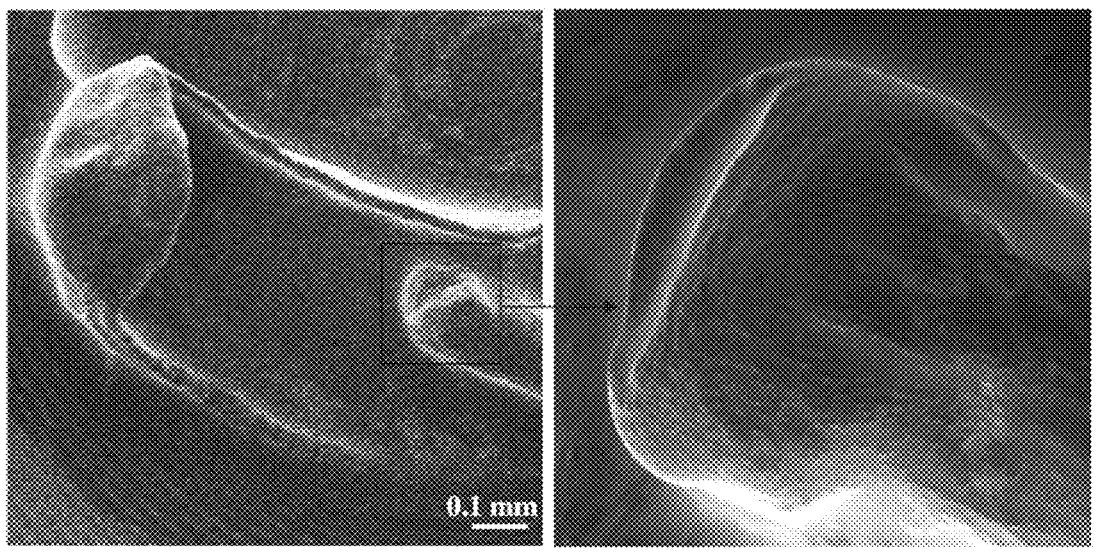
FIG. 10 is a photograph illustrating the situation of SEM video of Example 10.

Thereafter, the living planarian covered with a thin film was introduced in the sample chamber of a SEM, and videotaped (FIG. 10). The situation that the planarian was moving was observed even after the initiation of electron beam irradiation.

Moreover, the planarian was alive even after taken out from the sample chamber after SEM observation.

Example 11

Tween 20 was used as an amphiphilic compound. In order to prepare an independent thin film, Tween 20 of 50% (v/v) was dissolved in 100% ethanol, the resultant solution was spread on a glass plate using a spin coater (3000 rpm, 5 s) (SC8001, Aiden), and then subjected to a plasma polymerization. The thin film after polymerization was released from the glass plate in ethanol.

Figure 11:
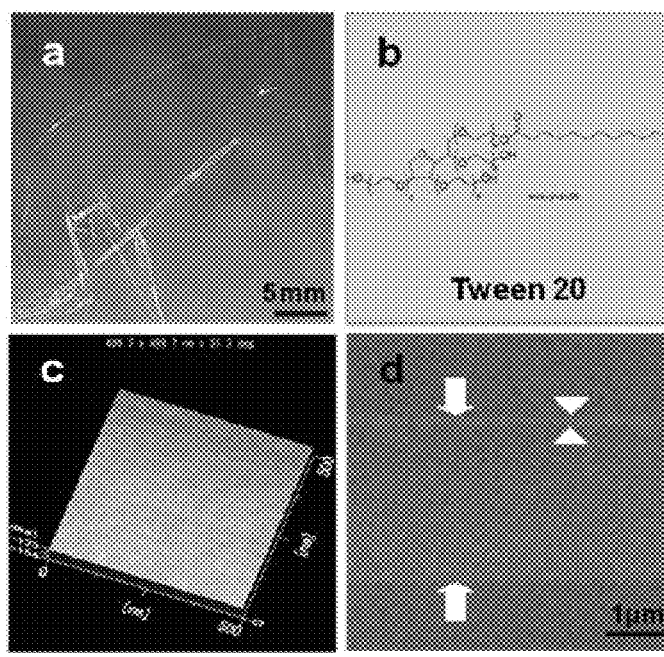
FIGS. 11(a) to 11(d) are photographs of a polymerized film of Example 11.

FIG. 11(*a*) is an optical microscopic image of the independent polymerized film (Tween 20) formed by plasma irradiation, FIG. 11(*b*) is the chemical formula of Tween 20, FIG. 11(*c*) is an AMF image of the film surface, and FIG. 11(*d*) is a TEM image of the cross section of the film. The distance between the arrows in FIG. 11(*d*) is the polymerized film of Tween 20. A thin layer is formed on the surface (the part between the arrowheads) of the irradiation side.

Next, a composition for evaporation suppression was prepared using a 1% aqueous solution of Tween 20 as an amphiphilic compound.

A living larva of wiggle tail was immersed in the composition for evaporation suppression for 1 minute, taken out therefrom, and the excess was wiped off, thereby covering the body surface of the living larva of wiggle tail with a thin film.

Figure 12:
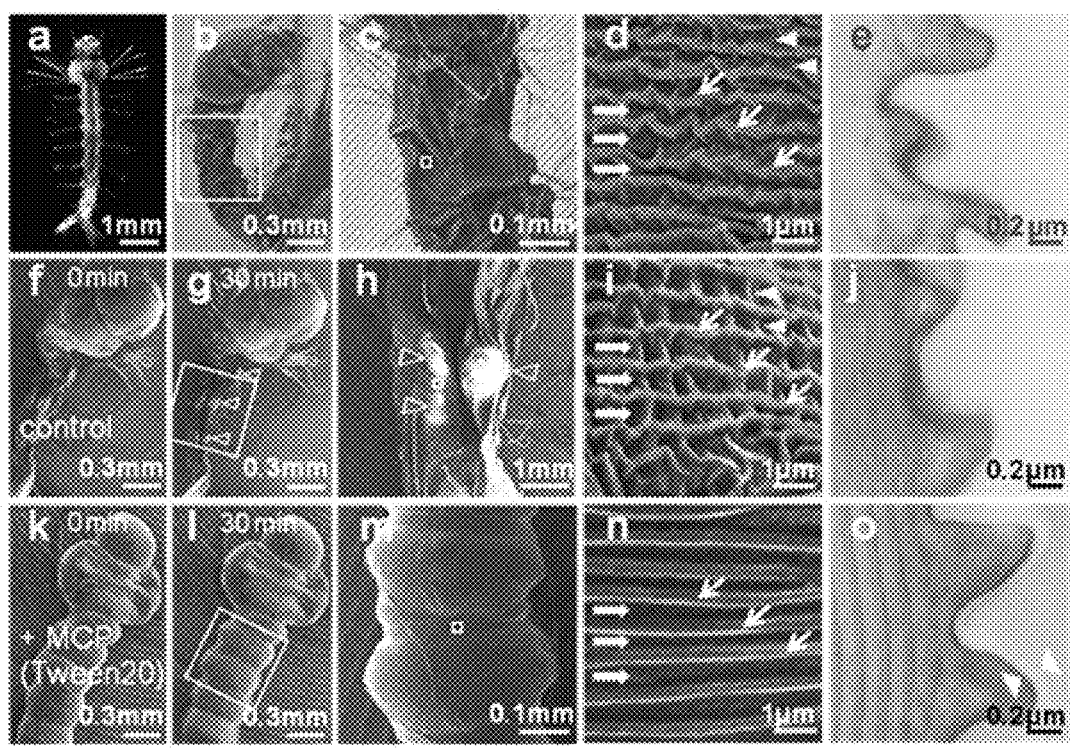
FIGS. 12(a) to 12(o) are photographs illustrating a polymerized film on the surface of a sample and the situation SEM video of Example 11.

Thereafter, the living larva of wiggle tail covered with a thin film was introduced in the sample chamber of a SEM, and videotaped (FIGS. 12(*a*) to 12(*o*)). The situation that the larva of wiggle tail was moving was observed even after the initiation of electron beam irradiation.

FIGS. 12(*a*) to 12(*o*) are SEM images of related art and novel SEM images of a sample coated with a plasma irradiated film (Tween 20). FIG. 12(*a*) is an optical microscopic image of wiggle tail, FIGS. 12(*b*) to 12(*d*) are SEM images of the related art, FIGS. 12(*f*) to 12(*n*) are individuals irradiated with plasma (without coating of Tween 20 (*f* to *i*) and with coating of Tween 20 (*k* to *n*)), and FIGS. 12(*e*), 12(*j*), and 12(*o*) are TEM images of the cross section of sample.

A living wiggle tail (*a*, time 0) was not irradiated with an electron beam, and a living wiggle tail (*b* to *d*, time 30) was irradiated with an electron beam for 30 minutes under high vacuum in a SEM. The arrowhead indicates the area of electrostatic charging.

In FIGS. 12(f) to (i), a living wiggle tail covered with 1% Tween 20 was irradiated with plasma for 3 minutes (f, time 0), and then observed by SEM for 30 minutes (g to i).

In FIGS. 12(k) to (n), a living wiggle tail was irradiated with an electron beam in a SEM of the related art (k is an optical microscopic image), and then observed (l to n).

The inside of each square of FIGS. 12(b), (g), and (l) was enlarged (c, h, and m), and then further enlarged (d, i, and n).

FIGS. 12(e, j, and o) are TEM images of the cross section of sample, and the layer between the arrowheads is a polymerized film formed by a plasma treatment.

Example 12

Triton™ X-100 was used as an amphiphilic compound. Triton™ X-100 of 1% (v/v) was dissolved in distilled water, the resultant solution was spread on a glass plate using a spin coater, and plasma polymerized, thereby obtaining an independent thin film in the same manner as in Example 11. FIG. 13(a) is an optical microscopic image of the independent polymerized film (Triton™ X-100) formed by plasma irradiation and FIG. 13(b) is the chemical formula of Triton™ X-100.

Next, a composition for evaporation suppression was prepared using a 1% aqueous solution of Triton™ X-100 as an amphiphilic compound.

A living larva of wiggle tail was immersed in the composition for evaporation suppression for 1 minute, taken out therefrom, and the excess was wiped off, thereby covering the body surface of the living larva of wiggle tail with a thin film.

Figure 13:
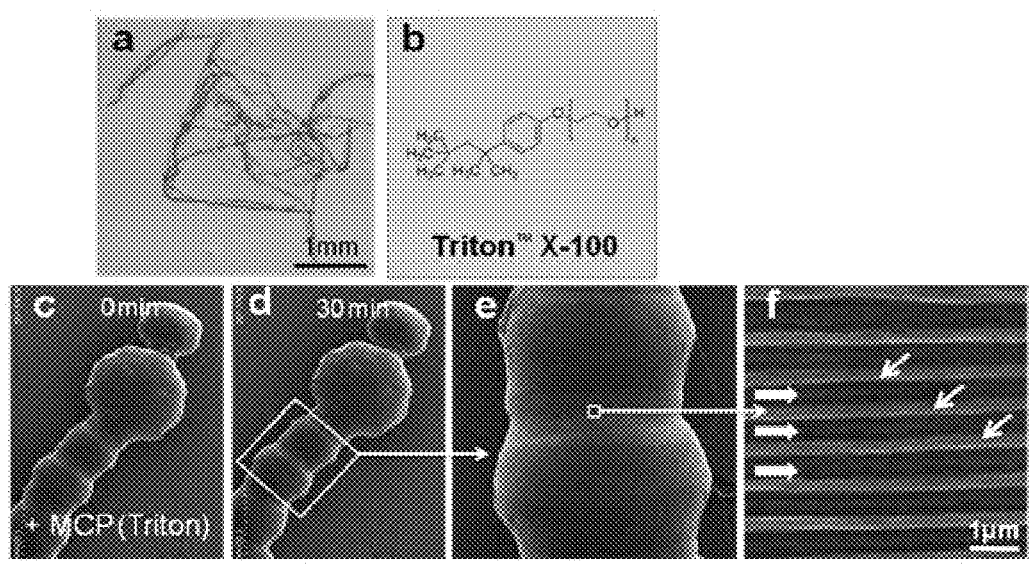
FIGS. 13(a) to 13(f) are photographs illustrating a polymerized film on the surface of a sample and the situation SEM video of Example 12.

Thereafter, the living larva of wiggle tail covered with a thin film was introduced in the sample chamber of a SEM, and videotaped (FIGS. 13(c) to 13(f)). FIG. 13(c) indicates the situation at 0 minute, FIG. 13 (d) indicates the situation at 30 minutes, and the inside of the square of FIG. 13 (d) was enlarged (FIG. 13 (e)) and further enlarged (FIG. 13 (f)). The situation that the larva of wiggle tail was moving was observed even after the initiation of electron beam irradiation.

Example 13

Pluronic® F-127 was used as an amphiphilic compound. Pluronic® F-127 of 1% (v/v) was dissolved in distilled water, the resultant solution was spread on a glass plate using a spin coater, and plasma polymerized, thereby obtaining an independent thin film in the same manner as in Example 11. FIG. 14(a) is an optical microscopic image of the independent polymerized film Pluronic® F-127 formed by plasma irradiation and FIG. 14(b) is the chemical formula of Pluronic® F-127.

Next, a composition for evaporation suppression was prepared using a 1% aqueous solution of Pluronic® F-127 as an amphiphilic compound.

A living larva of wiggle tail was immersed in the composition for evaporation suppression for 1 minute, taken out therefrom, and the excess was wiped off, thereby covering the body surface of the living larva of wiggle tail with a thin film.

Figure 14:
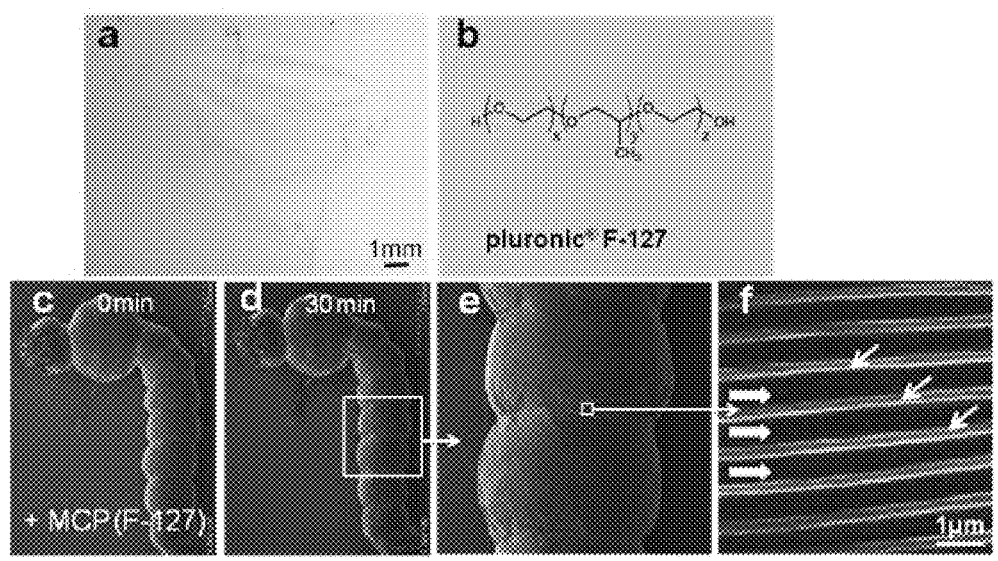
FIGS. 14(a) to 14(f) are photographs illustrating a polymerized film on the surface of a sample and the situation SEM video of Example 13.

Thereafter, the living larva of wiggle tail covered with a thin film was introduced in the sample chamber of a SEM, and videotaped (FIGS. 14(c) to 14(f)). FIG. 14(c) indicates the situation at 0 minute, FIG. 14 (d) indicates the situation at 30 minutes, and the inside of the square of FIG. 14 (d) was enlarged (FIG. 14(e)) and further enlarged (FIG. 14(f)). The situation that the larva of wiggle tail was moving was observed even after the initiation of electron beam irradiation.

Example 14

Brij® 35 was used as an amphiphilic compound. Brij® 35 of 1% (v/v) was dissolved in distilled water, the resultant solution was spread on a glass plate using a spin coater, and plasma polymerized, thereby obtaining an independent thin film in the same manner as in Example 11. FIG. 15(a) is an optical microscopic image of the independent polymerized film (Brij® 35) formed by plasma irradiation and FIG. 15(b) is the chemical formula of Brij® 35.

Next, a composition for evaporation suppression was prepared using a 1% aqueous solution of Brij® 35 as an amphiphilic compound.

A living larva of wiggle tail was immersed in the composition for evaporation suppression for 1 minute, taken out therefrom, and the excess was wiped off, thereby covering the body surface of the living larva of wiggle tail with a thin film.

Figure 15:
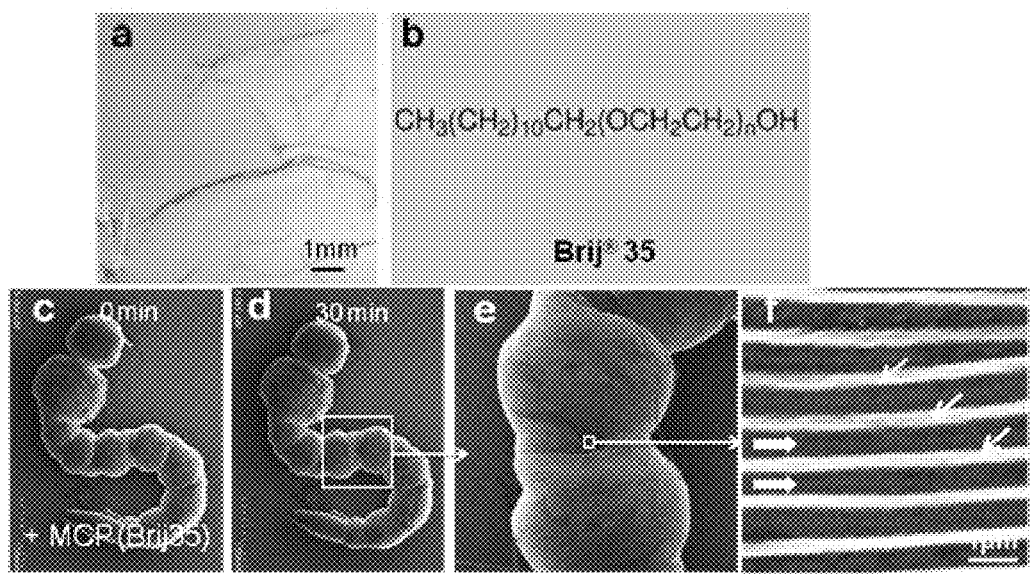
FIGS. 15(a) to 15(f) are photographs illustrating a polymerized film on the surface of a sample and the situation SEM video of Example 14.

Thereafter, the living larva of wiggle tail covered with a thin film was introduced in the sample chamber of a SEM, and videotaped (FIGS. 15(c) to 15(f)). FIG. 15(c) indicates the situation at 0 minute, FIG. 15 (d) indicates the situation at 30 minutes, and the inside of the square of FIG. 15 (d) was enlarged (FIG. 15(e)) and further enlarged (FIG. 15(f)). The situation that the larva of wiggle tail was moving was observed even after the initiation of electron beam irradiation.

Example 15

CHAPS was used as an amphiphilic compound. CHAPS of 1% (v/v) was dissolved in distilled water, the resultant solution was spread on a glass plate using a spin coater, and plasma polymerized, thereby obtaining an independent thin film in the same manner as in Example 11. FIG. 16(a) is an optical microscopic image of the independent polymerized film (CHAPS) formed by plasma irradiation and FIG. 16(b) is the chemical formula of CHAPS.

Next, a composition for evaporation suppression was prepared using a 1% aqueous solution of CHAPS as an amphiphilic compound.

A living larva of wiggle tail was immersed in the composition for evaporation suppression for 1 minute, taken out therefrom, and the excess was wiped off, thereby covering the body surface of the living larva of wiggle tail with a thin film.

Figure 16:
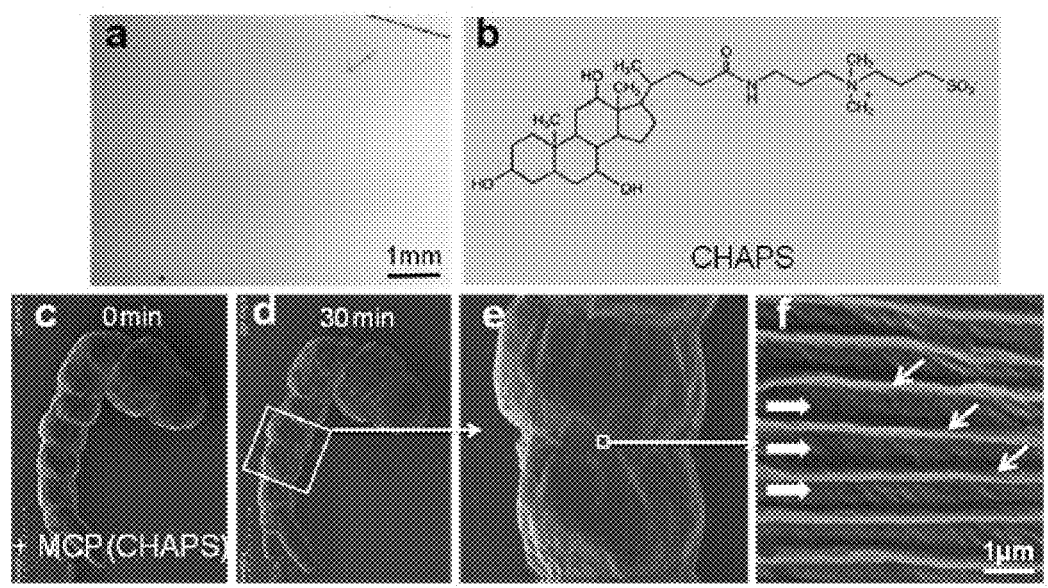
FIGS. 16(a) to 16(f) are photographs illustrating a polymerized film on the surface of a sample and the situation SEM video of Example 15.

Thereafter, the living larva of wiggle tail covered with a thin film was introduced in the sample chamber of a SEM, and videotaped (FIGS. 16(c) to 16(f)). FIG. 16(c) indicates the situation at 0 minute, FIG. 16 (d) indicates the situation at 30 minutes, and the inside of the square of FIG. 16 (d) was enlarged (FIG. 16(e)) and further enlarged (FIG. 16(f)). The situation that the larva of wiggle tail was moving was observed even after the initiation of electron beam irradiation.

Example 16

MEGA8 was used as an amphiphilic compound. MEGA8 of 1% (v/v) was dissolved in distilled water, the resultant solution was spread on a glass plate using a spin coater, and plasma polymerized, thereby obtaining an independent thin film in the same manner as in Example 11. FIG. 17(a) is an optical microscopic image of the independent polymerized film (MEGA8) formed by plasma irradiation and FIG. 17(b) is the chemical formula of MEGA8.

Next, a composition for evaporation suppression was prepared using a 1% aqueous solution of MEGA8 as an amphiphilic compound.

A living larva of wiggle tail was immersed in the composition for evaporation suppression for 1 minute, taken out therefrom, and the excess was wiped off, thereby covering the body surface of the living larva of wiggle tail with a thin film.

Figure 17:
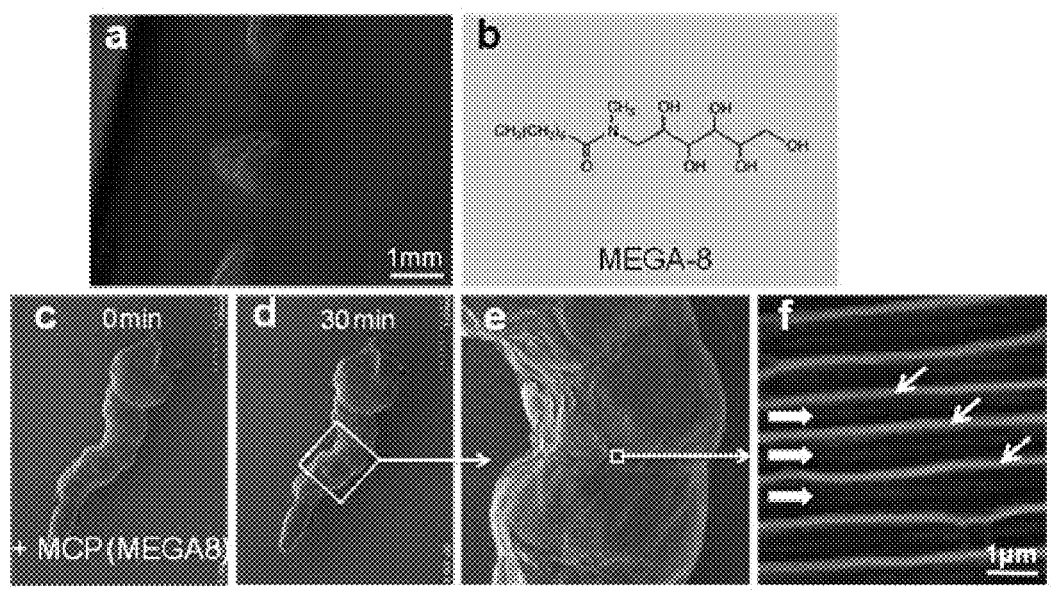
FIGS. 17(a) to 17(f) are photographs illustrating a polymerized film on the surface of a sample and the situation SEM video of Example 16.

Thereafter, the living larva of wiggle tail covered with a thin film was introduced in the sample chamber of a SEM, and videotaped (FIGS. 17(c) to 17(f)). FIG. 17(c) indicates the situation at 0 minute, FIG. 17 (d) indicates the situation at 30 minutes, and the inside of the square of FIG. 17 (d) was enlarged (FIG. 17(e)) and further enlarged (FIG. 17(f)). The situation that the larva of wiggle tail was moving was observed even after the initiation of electron beam irradiation.

Example 17

Sodium cholate was used as an amphiphilic compound. Sodium cholate of 1% (v/v) was dissolved in distilled water, the resultant solution was spread on a glass plate using a spin coater, and plasma polymerized, thereby obtaining an independent thin film in the same manner as in Example 11. FIG. 18(a) is an optical microscopic image of the independent polymerized film (sodium cholate) formed by plasma irradiation and FIG. 18(b) is the chemical formula of sodium cholate.

Next, a composition for evaporation suppression was prepared using a 1% aqueous solution of sodium cholate as an amphiphilic compound.

A living larva of wiggle tail was immersed in the composition for evaporation suppression for 1 minute, taken out therefrom, and the excess was wiped off, thereby covering the body surface of the living larva of wiggle tail with a thin film.

Figure 18:
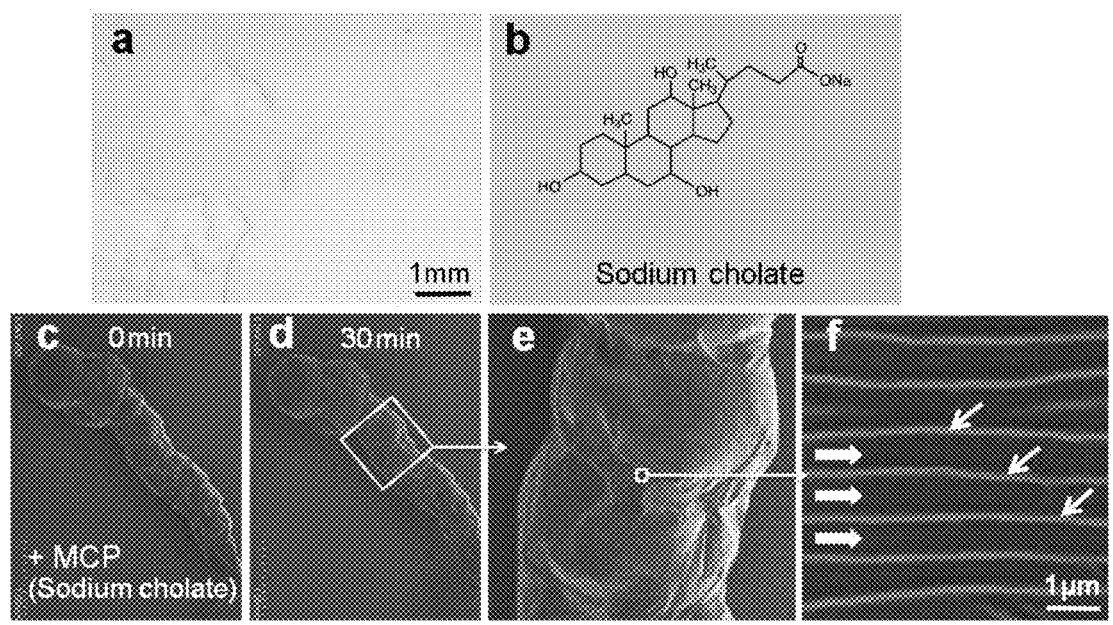
FIGS. 18(a) to 18(f) are photographs illustrating a polymerized film on the surface of a sample and the situation SEM video of Example 17.

Thereafter, the living larva of wiggle tail covered with a thin film was introduced in the sample chamber of a SEM, and videotaped (FIGS. 18(c) to 18(f)). FIG. 18(c) indicates the situation at 0 minute, FIG. 18 (d) indicates the situation at 30 minutes, and the inside of the square of FIG. 18 (d) was enlarged (FIG. 18(e)) and further enlarged (FIG. 18(f)). The situation that the larva of wiggle tail was moving was observed even after the initiation of electron beam irradiation.

Example 18 n-Dodecyl-β-D-maltoside was used as an amphiphilic compound. n-Dodecyl-β-D-maltoside of 1% (v/v) was dissolved in distilled water, the resultant solution was spread on a glass plate using a spin coater, and plasma polymerized, thereby obtaining an independent thin film in the same manner as in Example 11. FIG. 19(a) is an optical microscopic image of the independent polymerized film (n-dodecyl-β-D-maltoside) formed by plasma irradiation and FIG. 19(b) is the chemical formula of n-dodecyl-β-D-maltoside.

Next, a composition for evaporation suppression was prepared using a 1% aqueous solution of n-dodecyl-β-D-maltoside as an amphiphilic compound.

A living larva of wiggle tail was immersed in the composition for evaporation suppression for 1 minute, taken out therefrom, and the excess was wiped off, thereby covering the body surface of the living larva of wiggle tail with a thin film.

Figure 19:
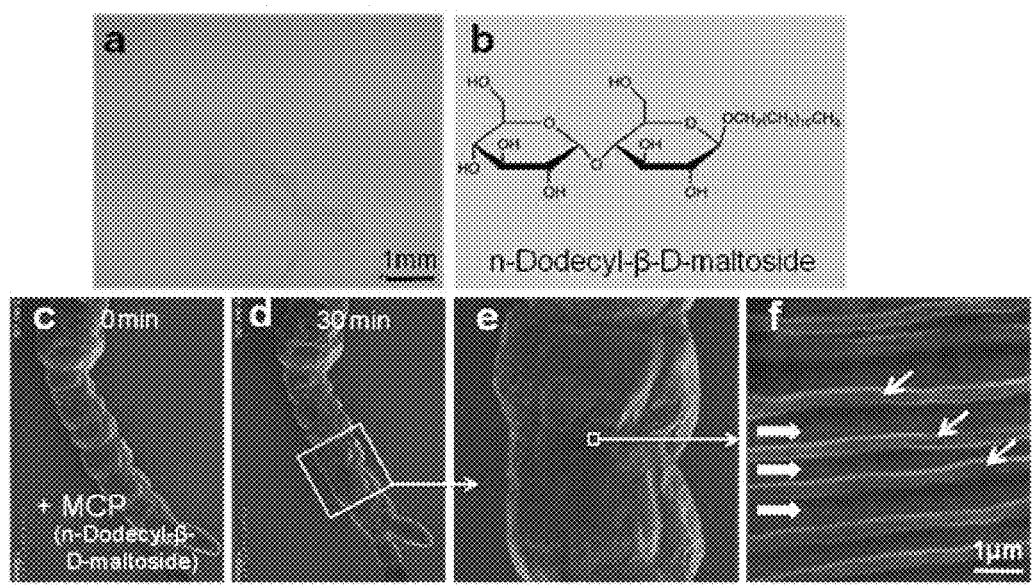
FIGS. 19(a) to 19(f) are photographs illustrating a polymerized film on the surface of a sample and the situation SEM video of Example 18.

Thereafter, the living larva of wiggle tail covered with a thin film was introduced in the sample chamber of a SEM, and videotaped (FIGS. 19(c) to 19(f)). FIG. 19(c) indicates the situation at 0 minute, FIG. 19 (d) indicates the situation at 30 minutes, and the inside of the square of FIG. 19 (d) was enlarged (FIG. 19(e)) and further enlarged (FIG. 19(f)). The situation that the larva of wiggle tail was moving was observed even after the initiation of electron beam irradiation.

Example 19 n-Octyl-β-D-glucoside was used as an amphiphilic compound. n-Octyl-β-D-glucoside of 1% (v/v) was dissolved in distilled water, the resultant solution was spread on a glass plate using a spin coater, and plasma polymerized, thereby obtaining an independent thin film in the same manner as in Example 11. FIG. 20(a) is an optical microscopic image of the independent polymerized film (n-octyl-β-D-glucoside) formed by plasma irradiation and FIG. 20(b) is the chemical formula of n-octyl-β-D-glucoside.

Next, a composition for evaporation suppression was prepared using a 1% aqueous solution of n-octyl-β-D-glucoside as an amphiphilic compound.

A living larva of wiggle tail was immersed in the composition for evaporation suppression for 1 minute, taken out therefrom, and the excess was wiped off, thereby covering the body surface of the living larva of wiggle tail with a thin film.

Figure 20:
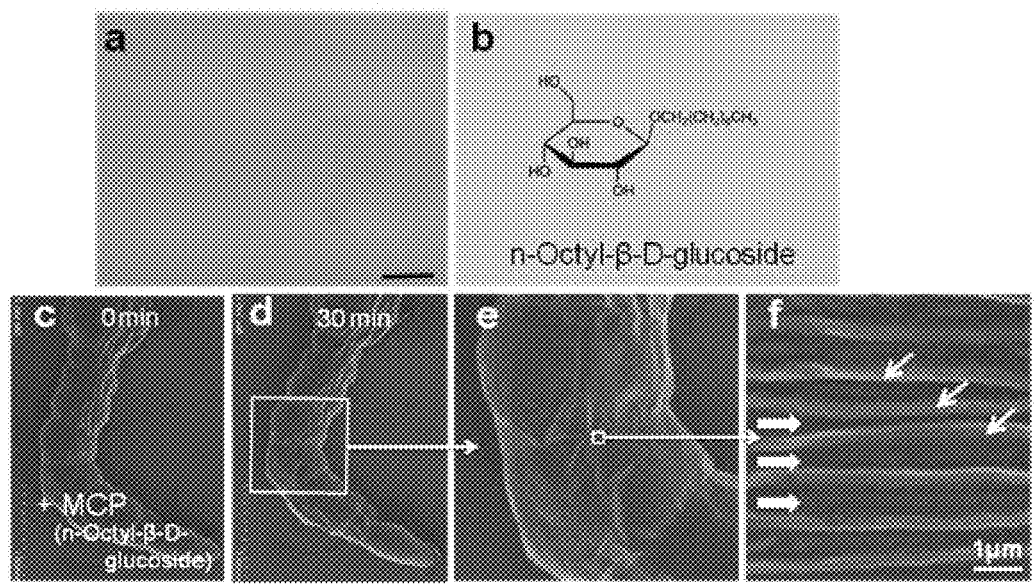
FIGS. 20(a) to 20(f) are photographs illustrating a polymerized film on the surface of a sample and the situation SEM video of Example 19.

Thereafter, the living larva of wiggle tail covered with a thin film was introduced in the sample chamber of a SEM, and videotaped (FIGS. 20(c) to 20(f)). FIG. 20(c) indicates the situation at 0 minute, FIG. 20 (d) indicates the situation at 30 minutes, and the inside of the square of FIG. 20 (d) was enlarged (FIG. 20(e)) and further enlarged (FIG. 20(f)). The situation that the larva of wiggle tail was moving was observed even after the initiation of electron beam irradiation.

Example 20

1,3-Diallylimidazolium bromide was used as an ionic liquid. 1,3-Diallylimidazolium bromide of 1% (v/v) was dissolved in distilled water, the resultant solution was spread on a glass plate using a spin coater, and plasma polymerized, thereby obtaining an independent thin film in the same manner as in Example 11. FIG. 20(a) is an optical microscopic image of the independent polymerized film (1,3-diallylimidazolium bromide) formed by plasma irradiation and FIG. 20(b) is the chemical formula of 1,3-diallylimidazolium bromide.

Next, a composition for evaporation suppression was prepared using a 1% aqueous solution of 1,3-diallylimidazolium bromide as an ionic liquid.

A living larva of wiggle tail was immersed in the composition for evaporation suppression for 1 minute, taken out therefrom, and the excess was wiped off, thereby covering the body surface of the living larva of wiggle tail with a thin film.

Figure 21:
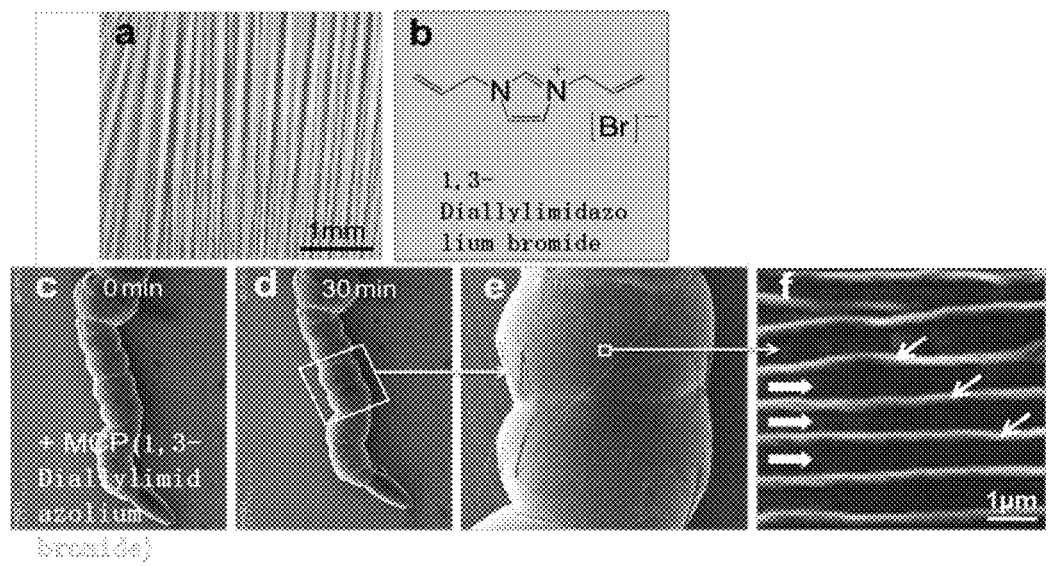
FIGS. 21(a) to 21(f) are photographs illustrating a polymerized film on the surface of a sample and the situation SEM video of Example 20.

Thereafter, the living larva of wiggle tail covered with a thin film was introduced in the sample chamber of a SEM, and videotaped (FIGS. 21(c) to (f)). FIG. 21(c) indicates the situation at 0 minute, FIG. 21 (*d*) indicates the situation at 30 minutes, and the inside of the square of FIG. 21 (*d*) was enlarged (FIG. 21(*e*)) and further enlarged (FIG. 21(*f*)). The situation that the larva of wiggle tail was moving was observed even after the initiation of electron beam irradiation.

REFERENCE SIGNS LIST

1 Scanning electron microscope (SEM)
2 Preliminary exhaust chamber
3 Sample exchange bar
4 Sample
5 Vacuum gauge
6 Control valve
7 Vacuum pump
8 Microscope body
9 Power source
10 Sample chamber
11 Sample folder
12 Glove box
13 Housing in glove box
14 Window part
15 Work port
16 Inert gas cylinder
17 Bell jar
18 Plasma irradiation device or electron beam irradiation device
19 Sample chamber inside
20 Sample stub
21 Three dimensional manipulator
22 Secondary electron detector
23 High speed color camera
24 Temperature regulator
25 Sensor
30 C-ring
31 O-ring
32 Polymerized film
33 Grid mesh
34 Cells

The invention claimed is:

1. A sample observation method by an electron microscope, the method comprising:
applying a composition for evaporation suppression including at least one kind selected from an amphiphilic compound, oils and fats, and an ionic liquid to a surface of a sample;
irradiating the sample applied with the composition for evaporation suppression with an electron beam or plasma to form a polymerized film on the surface of the sample as a thin film and covering the sample with the polymerized film; and
displaying an electron microscopic image of the sample covered with the polymerized film and accommodated in a sample chamber under vacuum on a display device.

2. The sample observation method by an electron microscope according to claim 1, wherein the polymerized film is formed on a surface of a sample as a thin film by a polymerization reaction by irradiating the sample with an electron beam for sample observation in the sample chamber of the electron microscope.

3. The sample observation method by an electron microscope according to claim 1, wherein the polymerized film is formed on a surface of a sample as a thin film by a polymerization reaction by irradiating the sample with an electron beam or plasma other than the electron beam for the sample observation of the electron microscope before the sample observation by the electron microscope.

4. The sample observation method by an electron microscope according to claim 1, wherein the composition for evaporation suppression includes at least one kind selected from an amphiphilic compound, a metal compound, and a saccharide.

5. The sample observation method by an electron microscope according to claim 1, wherein an electron microscopic image of a hydrated sample in a wet state is displayed on the displaying device without accompanying collapse of the hydrated sample.

6. The sample observation method by an electron microscope according to claim 1, the method comprising:
applying the composition for evaporation suppression to a body surface of a living biological sample to form a thin film, and covering the sample with the thin film; and
displaying an electron microscopic image of movement of the biological sample covered with the thin film and accommodated in a sample chamber under vacuum as it is alive on a display device.

7. The sample observation method by an electron microscope according to claim 6, wherein the biological sample is provided with motility by suppressing decrease in temperature associated with evaporation from the inside of the biological sample body, and the morphology of the biological sample is preserved as it is, by the thin film.

8. The sample observation method by an electron microscope according to claim 6, wherein an internal body temperature of the biological sample, which enables the biological sample to be active, is maintained even under vacuum by the thin film.

9. The sample observation method by an electron microscope according to claim 1, wherein the electron microscopic image of a sample is displayed on a display device without causing charge up of the sample using a scanning electron microscope.

10. A composition for evaporation suppression under vacuum, which is used to form a thin film on a surface of a sample including an evaporable substance under vacuum and cover the sample, and thus to impart barrier performance suppressing evaporation of the evaporable substance under vacuum to the evaporable substance, the composition comprising at least one kind selected from an amphiphilic compound, oils and fats, and an ionic liquid, wherein a polymerized film is formed on a surface of a sample as a thin film by irradiating the sample applied with the composition for evaporation suppression with an electron beam or plasma, and the sample is covered with the polymerized film.

11. The composition for evaporation suppression under vacuum according to claim 10, the composition being used to form a thin film on a surface of a living biological sample body and cover the biological sample, and thus to impart barrier performance suppressing evaporation of an evaporable substance under vacuum to the evaporable substance in the biological sample body.

12. The composition for evaporation suppression under vacuum according to claim 10, the composition comprising at least one kind selected from an amphiphilic compound, a metal compound, and a saccharide.

13. A scanning electron microscope, the scanning electron microscope comprising a preliminary exhaust chamber capable of being introduced with a sample to be mounted in a sample chamber in a microscope body, and an exhauster deaerating the sample chamber and the preliminary exhaust chamber, wherein the scanning electron microscope is used in a method comprising the steps of applying a composition for evaporation suppression including at least one kind selected from an amphiphilic compound, oils and fats, and an ionic liquid to a surface of a sample;

irradiating the sample applied with the composition for evaporation suppression with an electron beam or plasma to form a polymerized film on the surface of the sample as a thin film and covering the sample with the polymerized film; and displaying an electron microscopic image of the sample covered with the polymerized film and accommodated in a sample chamber under vacuum on a display device.

14. The scanning electron microscope according to claim 13, wherein the preliminary exhaust chamber is equipped with a glove box.

15. The scanning electron microscope according to claim 13, wherein the sample chamber or the preliminary exhaust chamber is equipped with a plasma irradiation device or an electron beam irradiation device.

16. The scanning electron microscope according to claim 13, wherein the sample chamber or the preliminary exhaust chamber is equipped with a three dimensional manipulator capable of operating on a sample.

17. The scanning electron microscope according to 13, wherein the sample chamber is equipped with a detection position regulatory mechanism capable of three dimensionally regulating a relative position of a secondary electron detector and a sample.

18. The scanning electron microscope according to claim 13, wherein the sample chamber is equipped with a high speed color camera capable of acquiring color information of a sample.

19. The scanning electron microscope according to claim 13, the scanning electron microscope comprising a temperature regulator capable of regulating a temperature of a sample stub in a sample chamber.

20. The scanning electron microscope according to claim 13, wherein the sample chamber is equipped with at least one sensor selected from an electrical sensor, a light sensor, a gas sensor, a water sensor, and a temperature sensor.

21. A transmission electron microscope, the transmission electron microscope comprising a preliminary exhaust chamber capable of being introduced with a sample to be mounted in a sample chamber in a microscope body, and an exhauster deaerating the sample chamber and the preliminary exhaust chamber, wherein the transmission electron microscope is used in a method comprising the steps of applying a composition for evaporation suppression including at least one kind selected from an amphiphilic compound, oils and fats, and an ionic liquid to a surface of a sample;

irradiating the sample applied with the composition for evaporation suppression with an electron beam or plasma to form a polymerized film on the surface of the sample as a thin film and covering the sample with the polymerized film; and displaying an electron microscopic image of the sample covered with the polymerized film and accommodated in a sample chamber under vacuum on a display device.

22. The transmission electron microscope according to claim 21, wherein the preliminary exhaust chamber is equipped with a glove box.

23. The transmission electron microscope according to claim 21, wherein the sample chamber or the preliminary exhaust chamber is equipped with a plasma irradiation device or an electron beam irradiation device.

24. The transmission electron microscope according to claim 21, wherein each of both sides of a grid mesh to be mounted with a sample includes a polymerized film formed by irradiating the composition for evaporation suppression with an electron beam or plasma.

* * * * *